United States Patent [19]

Kitano et al.

[11] Patent Number: 5,624,917
[45] Date of Patent: Apr. 29, 1997

[54] METHOD OF INHIBITING SQUALENE SYNTHETASE

[75] Inventors: Kazuaki Kitano, Sakai; Takashi Sohda, Takatsuki; Ryuichi Tozawa, Ibaraki; Hitoshi Ikeda, Higashiosaka; Tsuneo Oda, Kyoto, all of Japan

[73] Assignee: Takeda Chemical Industries, Ltd., Osaka, Japan

[21] Appl. No.: 585,754

[22] Filed: Jan. 16, 1996

Related U.S. Application Data

[63] Continuation of Ser. No. 971,611, Nov. 5, 1992, abandoned.

[30] Foreign Application Priority Data

Nov. 6, 1991 [JP] Japan .................... 3-289593
Oct. 5, 1992 [JP] Japan .................... 4-265895

[51] Int. Cl.$^6$ ............ A61K 31/675; A61K 31/685; A61K 31/66
[52] U.S. Cl. .............. 514/76; 514/86; 514/102; 514/107; 544/243; 548/112; 548/119; 558/158; 562/13
[58] Field of Search ................ 514/76, 86, 107, 514/108; 544/112, 119; 558/158; 562/13

[56] References Cited

U.S. PATENT DOCUMENTS

| | | | |
|---|---|---|---|
| 4,096,208 | 6/1978 | Dursch et al. | |
| 4,416,877 | 11/1983 | Bentzen | 424/204 |
| 4,639,338 | 1/1987 | Stahl et al. | 562/13 |
| 4,719,203 | 1/1988 | Bosies et al. | |
| 4,746,654 | 5/1988 | Breliere et al. | |
| 4,876,247 | 10/1989 | Barbier et al. | 514/89 |
| 4,876,248 | 10/1989 | Breliere et al. | 562/13 X |
| 4,927,814 | 5/1990 | Gall et al. | 562/13 X |
| 4,933,472 | 6/1990 | Isomura et al. | 562/13 X |
| 4,970,335 | 11/1990 | Isomura et al. | 562/13 |
| 5,036,058 | 7/1991 | Jaeggi | 562/13 X |
| 5,154,843 | 10/1992 | Rizvi et al. | 562/13 X |
| 5,157,027 | 10/1992 | Biller et al. | |
| 5,162,310 | 11/1992 | Jaeggi | 562/13 X |
| 5,280,022 | 1/1994 | Sohda et al. | 514/114 |
| 5,281,748 | 1/1994 | Jaeggi | 562/13 |
| 5,376,647 | 12/1994 | Sohda et al. | 514/89 |

FOREIGN PATENT DOCUMENTS

| | | |
|---|---|---|
| 0151072 | 8/1985 | European Pat. Off. |
| 0230068 | 7/1987 | European Pat. Off. |
| 0243173 | 10/1987 | European Pat. Off. |
| 0282320 | 9/1988 | European Pat. Off. |
| 0282309 | 9/1988 | European Pat. Off. |
| 0298553 | 1/1989 | European Pat. Off. |
| 0325482 | 7/1989 | European Pat. Off. |
| 0324421 | 7/1989 | European Pat. Off. |
| 0337706 | 10/1989 | European Pat. Off. |
| 0339237A2 | 11/1989 | European Pat. Off. |
| 0418064A2 | 3/1991 | European Pat. Off. |
| 0464509 | 1/1992 | European Pat. Off. |
| 0491374 | 6/1992 | European Pat. Off. |
| 0513761A2 | 11/1992 | European Pat. Off. |
| 0513760 | 11/1992 | European Pat. Off. |
| 0609440A1 | 8/1994 | European Pat. Off. |
| 54-37829 | 3/1979 | Japan . |
| 1258695 | 10/1989 | Japan . |
| 445675 | 3/1975 | U.S.S.R. |

OTHER PUBLICATIONS

Chem. Abstr. 1979, 91(13), 103762; JP54037829 publ. Mar. 20, 1979.
Journal of Medicinal Chemistry, vol. 31, No. 10, pp. 1869–1871 (1988).

Primary Examiner—Robert W. Ramsuer
Assistant Examiner—Michael G. Ambrose
Attorney, Agent, or Firm—Foley & Lardner

[57] ABSTRACT

There is provided a squalene inhibitory composition containing a 1,1-bisphosphonic acid compound, a lower alkyl ester thereof, or a salt thereof, which is useful for treating hypercholesterolemia. There are also provided novel compounds having squalene synthetase inhibitory activity and a pharmaceutical composition for treating hypercholesterolemia containing a 1,1-bisphosphonic compound, a lower alkyl ester thereof or a salt thereof.

24 Claims, No Drawings

METHOD OF INHIBITING SQUALENE SYNTHETASE

This application is a continuation of application Ser. No. 07/971,611, filed Nov. 5, 1992, now abandoned.

FIELD OF THE INVENTION

The present invention relates to a squalene synthetase inhibitory composition comprising a 1,1-bisphosphonic acid compound, lower alkyl ester thereof or salt thereof which is useful for treating hypercholesterolemia.

BACKGROUND OF THE INVENTION

Hypercholesterolemia together with hypertension and smoking are known to be three major risk factors of ischemic heart disease. It is extremely important to control the cholesterol level in blood for prevention or treatment of coronary arteriosclerotic diseases as well as ischemic heart diseases.

With regard to medicaments to lower the cholesterol level in blood, attention has been paid to medicaments such as Cholestyramine, Colestipol and the like which capture bile acid and inhibit its absorption (disclosed, for example, in U.S. Pat. No. 4,027,009), medicaments such as Melinamide and the like which inhibit acyl coenzyme A cholesterol acyltransferase (ACAT) to inhibit absorption of cholesterol to intestine (disclosed in French Patent No. 1476596) and medicaments which inhibit biosynthesis of cholesterol.

As the inhibitor of biosynthesis of cholesterol, in particular, Lovastatin (disclosed in U.S. Pat. No. 4,231,938), Simvaststin (disclosed in U.S. Pat. No. 4,444,784), Pravastatin (disclosed in U.S. Pat. No. 4,346,227) and the like which inhibit 3-hydroxy-3-methylglutaryl coenzyme A (HMG-CoA) reductase have been used as the drug. However, when HMG-CoA reductase is inhibited, biosynthesis of not only cholesterol but also other components required for living bodies such as ubiquinone, dolichol, heme A and the like is inhibited. Then, there is a fear of side effects caused by the inhibition.

It is known that ubiquinone, dolichol, heme A and the like are synthesized from farnesyl pyrophosphate which is present in the pathway of cholesterol biosynthesis. Therefore, in order to prevent side effects caused by the loss of them, it is preferable to inhibit enzyme systems after farnesyl pyrophosphate in the pathway of cholesterol biosynthesis. Examples of such an enzyme includes squalene synthetase.

As squalene synthetase inhibitors, isoprenoid (phosphinylmethyl) phosphonate (Journal of Medicinal Chemistry, Vol. 31, No. 10, pp.1869 to 1871, 1988) and its derivatives (JP-A 1-213288, etc.) have been known. However, these compounds are not yet satisfactory in activities.

OBJECTS OF THE INVENTION

The main object of the present invention is to provide a novel squalene synthetase inhibitory composition.

This object as well as other objects and advantages of the present invention will become apparent to those skilled in the art from the following description.

SUMMARY OF THE INVENTION

The present inventors have intensively continued screening tests seeking for excellent squalene synthetase inhibitors. As a result, unexpectedly, it has been found that 1,1-bisphosphonic acid compounds which have been known to have bone resorption inhibitory activity, antiinflammatory activity, antirheumatic activity or herbicidal or fungicidal activity (JP-A 1-258695, EP-A-325482, EP-A-282309, EP-A-282320, EP-A-0337706, U.S. Pat. No. 4,746,654, EP-A-0151072, JP-A 54-37829, EP-A-298553, EP-A-230068, EP-A-243173, etc.) have squalene synthetase inhibitory activity and remarkably inhibit the biosynthesis of cholesterol. Thus, the present invention has been completed.

That is, the present invention provides a squalene synthetase inhibitory composition comprising a 1,1-bisphosphonic acid compound, a lower alkyl ester thereof or a salt thereof.

Specifically, the 1,1-bisphosphonic acid compound is represented by the general formula (I):

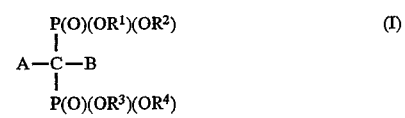

wherein $R^1$, $R^2$, $R^3$ and $R^4$ is hydrogen or lower alkyl, A is hydrogen, halogen, nitro, an optionally substituted hydrocarbon group, an optionally substituted heterocyclic group, optionally substituted acyl, optionally substituted amino, optionally substituted hydroxy, optionally substituted thiol, Ra—SO—, Ra—SO$_2$—, Ra—CS— (wherein Ra is an optionally substituted hydrocarbon group) or optionally substituted carboxyl, B is hydrogen, halogen, an optionally substituted hydrocarbon group, an optionally substituted heterocyclic group or optionally substituted carboxyl.

The present invention also provides a pharmaceutical composition for treating hypercholesterolemia comprising a 1,1-bisphosphonic acid compound, a lower alkyl ester thereof or a salt thereof.

DETAILED DESCRIPTION OF THE INVENTION

The 1,1-bisphosphonic acid compound in the present invention means a methylenebisphosphonic acid compound.

The 1,1-bisphosphonic acid compound of the above general formula (I) is specifically a compound of the general formula (II):

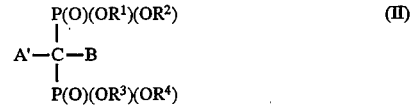

wherein

A' is hydrogen, halogen, nitro, an optionally substituted hydrocarbon group, an optionally substituted heterocyclic group, optionally substituted acyl, optionally substituted amino, optionally substituted hydroxy, optionally substituted thiol, Ra—SO—, Ra—SO$_2$— (wherein Ra is an optionally substituted hydrocarbon group) or optionally substituted carboxyl, and the other symbols are as defined above;

more specifically a compound of the general formula (III):

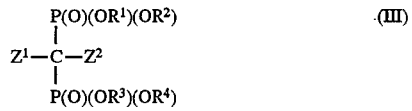

wherein $Z^1$ is an optionally substituted hydrocarbon group, an optionally substituted heterocyclic group, optionally substituted acyl, optionally substituted amino, optionally substituted thiol, Ra—SO$_2$— or Ra—CS— (wherein Ra is optionally substituted hydrocarbon group), $Z^2$ is hydrogen, hydroxy, halogen or optionally substituted amino, and the other symbols are as defined above;

more specifically a compound of the general formula (IV):

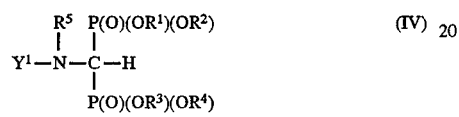

wherein $Y^1$ is optionally substituted $C_{1-20}$ alkyl, optionally substituted $C_{2-20}$ alkenyl, optionally substituted $C_{6-14}$ aryl, optionally substituted $C_{7-19}$ aralkyl, optionally substituted acyl, an optionally substituted heterocyclic group, an amino acid residue or peptidyl comprising 2 to 100 amino acids, $R^5$ is hydrogen or lower alkanoyl, and the other symbols are as defined above;

more specifically a compound of the general formula (V):

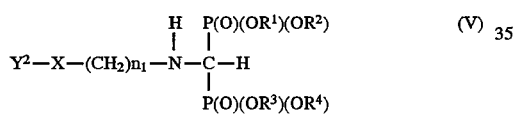

wherein $Y^2$ is optionally substituted straight or branched $C_{1-7}$ alkyl, optionally substituted $C_{3-7}$ cycloalkyl, optionally substituted $C_{6-14}$ aryl or an optionally substituted heterocyclic group, X is oxygen or optionally oxidized sulfur, $n_1$ is an integer of 1 to 20, and the other symbols are as defined above.

Other specific examples of the 1,1-bisphosphonic acid compound include a compound of the general formula (VI):

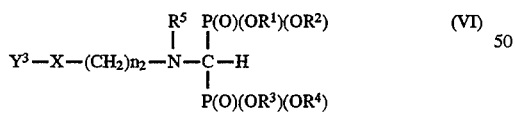

wherein $Y^3$ is an optionally substituted cyclic group, $n_2$ is an integer of 2 to 15, and the other symbols are as defined above;

a compound of the general formula (VII):

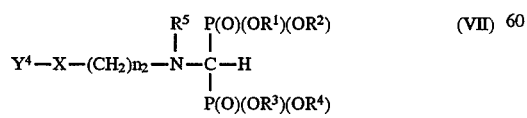

wherein $Y^4$ is optionally substituted alkyl, and the other symbols are as defined above;

a compound of the general formula (VIII):

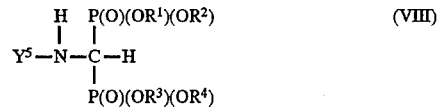

wherein $Y^5$ is $C_{5-20}$ alkyl, and the other symbols are as defined above;

a compound of the general formula (IX):

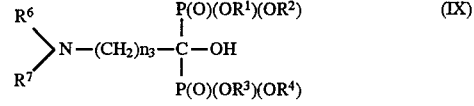

wherein $R^6$ and $R^7$ are the same or different and are an optionally substituted hydrocarbon group, $n_3$ is an integer of 2 to 10, and the other symbols are as defined above;

a compound of the general formula (X):

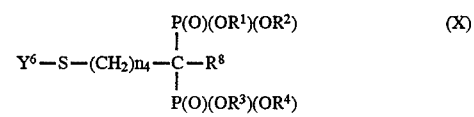

wherein $R^8$ is hydrogen or hydroxy, $Y^6$ is hydrogen, optionally substituted alkyl or optionally substituted phenyl, $n_4$ is a whole number of 0 to 10 ($n_4$ is not 0 when $R^8$ is hydroxy), and the other symbols are as defined above;

a compound of the general formula (XI):

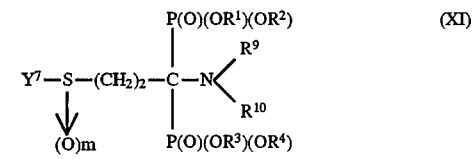

wherein $R^9$ is hydrogen, $C_{1-6}$ alkyl or —CONH$_2$, $R^{10}$ is hydrogen, $C_{1-6}$ alkyl, benzyl or optionally substituted phenyl, $Y^7$ is straight or branched $C_{1-6}$ alkyl, $C_{5-7}$ cycloalkyl, optionally substituted phenyl or an optionally substituted 5 or 6 membered heterocyclic group, m is a whole number of 0 to 2, and the other symbols are as defined above;

a compound of the general formula (XII):

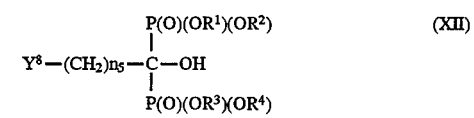

wherein $Y^8$ is an optionally substituted heterocyclic group, $n_5$ is an integer of 2 to 6, and the other symbols are as defined above;

a compound of the general formula (XIII):

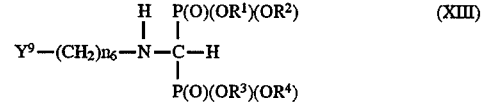

wherein $Y^9$ is an optionally substituted cyclic group, $n_6$ is an whole number of 0 to 15, and the other symbols are as defined above;

a compound of the general formula (XIV):

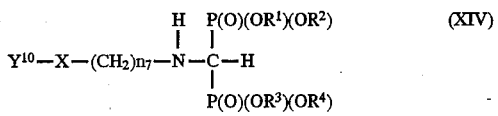

wherein
$Y^{10}$ is phenyl, pyridyl or pyrimidinyl, $n_7$ is an integer of 4 to 12, and the other symbols are as defined above;

a compound of the general formula (XV):

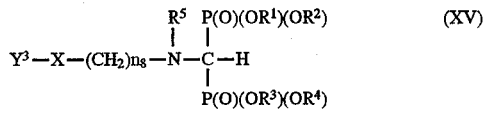

wherein
$n_8$ is an integer of 11 to 15 and the other symbols are as defined above, or a salt thereof;

a compound of the general formula (XVI):

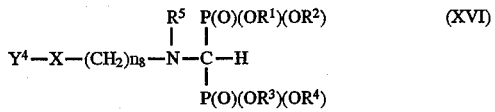

wherein
each symbol is as defined above, or a salt thereof; and a compound of the general formula (XXXII):

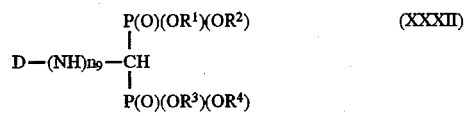

wherein
D is an optionally substituted hydrocarbon group, $n_9$ is 0 or 1, and the other symbols are as defined above.

As the lower alkyl in the lower alkyl ester of the 1,1-bisphosphonic acid compound and the lower alkyl represented by $R^1$, $R^2$, $R^3$ and $R^4$ in the above general formula, there is straight or branched alkyl having 1 to 4 carbon atoms such as methyl, ethyl, propyl, butyl, isobutyl, tert-butyl and the like.

As the halogen represented by A, A', B and $Z^2$ and the halogen used in the present specification, there are fluorine, chlorine, bromine and iodine.

Examples of the optionally substituted hydrocarbon group represented by A, A', B, $Z^1$, $R^6$, $R^7$, Ra and D include alkyl, alkenyl, aryl and the like.

Examples of the above alkyl include straight or branched $C_{1-20}$ alkyl such as methyl, ethyl, propyl, isopropyl, butyl, isobutyl, sec-butyl, tert-butyl, pentyl, isopentyl, neopentyl, hexyl, heptyl, octyl, nonyl, decyl, undecyl, dodecyl, tridecyl, tetradecyl, pentadecyl, hexadecyl, heptadecyl, octadecyl, nonadecyl, icosanyl and the like as well as $C_{3-7}$ cycloalkyl such as cyclopropyl, cyclobutyl, cyclohexyl, cycloheptyl and the like.

Examples of the above alkenyl include that having 2 to 20 carbon atoms such as allyl, vinyl, crotyl, 2-penten-1-yl, 3-penten-1-yl, 2-hexen-1-yl, 3-hexen-1-yl, 2-cyclohexenyl, 2-cyclopentenyl, 2-methyl-2-propen-1-yl, 3-methyl-2-buten-1-yl and the like.

The above alkyl and alkenyl exemplifying the hydrocarbon group represented by A, A', B, $Z^1$, $R^6$, $R^7$, Ra and D may be substituted with 1 to 4 substituents such as halogen, nitro, cyano, $C_{6-14}$ aryl (e.g., phenyl, naphthyl, anthryl, etc.), a heterocyclic group, optionally substituted acyl, optionally substituted amino, optionally substituted hydroxy, optionally substituted thiol, Rb—SO— (wherein Rb is as defined in Ra), Rc—$SO_2$— (wherein Rc is as defined in Ra) and optionally substituted carboxyl.

As the heterocyclic group as well as acyl, amino, hydroxy, thiol and carboxyl each of which may be substituted, there are the same groups as those represented by A hereinafter.

The above aryl exemplifying the hydrocarbon group represented by A, A', B, $Z^1$, $R^6$, $R^7$ and Ra is preferably that having 6 to 14 carbon atoms such as phenyl, naphthyl, anthryl, phenanthryl or the like.

The above aryl exemplifying the hydrocarbon group represented by A, A', B, $Z^1$, $R^6$, $R^7$, Ra and D may be substituted with 1 to 4 substituents such as halogen; nitro; cyano; straight or branched $C_{1-7}$ alkyl (e.g., methyl, ethyl, propyl, etc.) or $C_{3-7}$ cycloalkyl (e.g., cyclopropyl, cyclopentyl, cyclohexyl, etc.) each of which may be substituted with 1 to 3 substituents such as halogen, hydroxy and $C_{1-6}$ alkoxy (e.g., methoxy, ethoxy, propoxy, etc.); $C_{6-14}$ aryl (e.g., phenyl, naphthyl, anthryl, etc.); a heterocyclic group; optionally substituted acyl; optionally substituted amino; optionally substituted hydroxy; optionally substituted thiol; Rd-SO— (wherein Rd is as defined in Ra); Re—$SO_2$— (wherein Re is as defined in Ra) and optionally substituted carboxyl.

As the heterocyclic group as well as acyl, amino, hydroxy, thiol and carboxyl each of which may be substituted, there are the same groups as those represented by A hereinafter.

Among the hydrocarbon group represented by D, the group of the general formula:

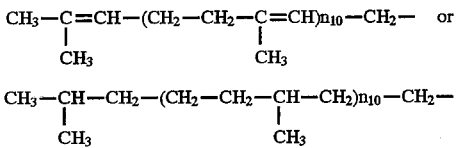

wherein $n_{10}$ is an integer of 1 to 3 is preferred.

Examples of the heterocycle in the optionally substituted heterocyclic group represented by A, A', B, $Z^1$ and $Y^8$ include 5 to 7 membered heterocycles containing one sulfur atom, nitrogen atom or oxygen atom; 5 to 6 membered heterocycles containing 2 to 4 nitrogen atoms; 5 to 6 membered heterocycles containing 1 to 2 nitrogen atoms and one sulfur atom or oxygen atom; and the like. These heterocycles may form a condensed ring with a 6 membered ring containing 1 to 2 nitrogen atoms, benzene ring or 5 membered ring containing one sulfur atom.

Specific examples of the heterocyclic group include 2-pyridyl, 3-pyridyl, 4-pyridyl, pyrimidinyl, pyrazinyl, pyridazinyl, pyrazolyl, imidazolyl, thiazolyl, isothiazolyl, oxazolyl, isoxazolyl, pyrido[2,3-d]pyrimidinyl, benzopyranyl, 1,8-naphthyridyl, 1,5-naphthyridyl, 1,6-naphthyridyl, 1,7-naphthyridyl, quinolyl, theno[2,3-b]pyridyl, tetrazolyl, thiadiazolyl, oxadiazolyl, triazinyl, triazolyl, thienyl, pyrrolyl, pyrrolinyl, furyl, pyrrolidinyl, benzothienyl, indolyl, imidazolidinyl, piperidyl, piperidino, piperazinyl, morpholinyl, morpholino and the like.

Examples of the substituent of the heterocyclic group include the same substituents as those of the above optionally substituted aryl exemplifying the optionally substituted hydrocarbon group represented by A.

Examples of the 5 or 6 membered heterocyclic group in the optionally substituted 5 or 6 membered heterocyclic group represented by $Y^7$ include 5 or 6 membered heterocyclic groups in the above heterocyclic groups represented by A. Examples of the substituents include the same substituents as those of the above heterocyclic group represented by A.

Examples of the acyl in the optionally substituted acyl represented by A, A' and $Z^1$ include organic carboxylic acid acyl, sulfonic acid acyl having a $C_{1-6}$ hydrocarbon group [e.g., $C_{1-6}$ alkyl (e.g., methyl, ethyl, n-propyl, isopropyl, hexyl, etc.), phenyl, etc.] and the like. Examples of the organic carboxylic acid acyl include formyl, $C_{1-10}$ alkyl-carbonyl (e.g., acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, etc.), $C_{2-10}$ alkenyl-carbonyl (e.g., crotonyl, 2-cyclohexenecarbonyl, etc.), $C_{6-14}$ aryl-carbonyl (e.g., benzoyl, etc.), $C_{7-19}$ aralkyl-carbonyl (e.g., phenylacetyl, etc.), 5 or 6 membered aromatic heterocycle carbonyl (e.g., nicotinoyl, 4-thiazolylcarbonyl, etc.), 5 or 6 membered aromatic heterocycle acetyl (e.g., 3-pyridylacetyl, 4-thiazolylacetyl, etc.), amino acid residues and peptidyl comprising 2 to 100 amino acids. Examples of the sulfonic acid acyl having a $C_{1-6}$ hydrocarbon group include straight or branched $C_{1-6}$ alkylsulfonyl such as methanesulfonyl, ethanesulfonyl and the like. These organic carboxylic acid acyl and sulfonic acid acyl may be substituted with 1 to 3 substituents such as the above halogen, hydroxy, $C_{1-6}$ alkoxy, amino or the like. Specific examples of the substituted acyl include trifluoroacetyl, 3-cyclohexyloxypropionyl, 4-chlorobenzoyl, 6-chloronicotinoyl, 2-methyl-4-phenyl-5-thiazolylacetyl and the like. The amino acid in the above amino acid residue and the amino acid constituting the above peptidyl may be any amino acid which has an amino group and a carboxyl group. It is preferably a natural amino acid. The amino acid residue in the present invention is preferably the group obtained by dropping an OH group of the C-terminus of these amino acids or peptides.

Examples of the substituent in the substituted amino represented by A, A', $Z^1$ and $Z^2$ include groups defined as $Y^1$ and $R^5$ in the general formula (IV). The substituents may be the same or different.

As the $C_{1-20}$ alkyl, $C_{2-20}$ alkenyl, $C_{6-14}$ aryl, acyl, heterocyclic group, amino acid residue and peptidyl comprising 2 to 100 amino acids (group obtained by dropping hydrogen of the N-terminus of the amino acid or peptide) represented by $Y^1$, there are the same groups as those described above. Examples of the $C_{7-19}$ aralkyl include benzyl, naphthylethyl, trityl and the like.

Examples of the substituent of the $C_{2-20}$ alkenyl, $C_{7-19}$ aralkyl and acyl each of which may be substituted represented by $Y^1$ include halogen, $C_{1-6}$ alkoxy (e.g., methoxy, ethoxy, propoxy, etc.), mono- or di-($C_{1-6}$ alkoxy)phosphoryl (e.g., methoxyphosphoryl, ethoxyphosphoryl, dimethoxyphosphoryl, etc.), phosphono and the like. The number of the substituent is preferably 1 to 3.

Examples of the substituent in the optionally substituted $C_{6-14}$ aryl represented by $Y^1$ include the same substituents as those in the optionally substituted $C_{6-14}$ aryl represented by $Y^2$ hereinafter.

Examples of the substituent in the optionally substituted heterocyclic group represented by $Y^1$ include halogen, $C_{1-10}$ alkyl (e.g., methyl, ethyl, propyl, etc.), $C_{3-10}$ cycloalkyl (e.g., cyclopropyl, cyclopentyl, cyclohexyl, etc.), $C_{2-10}$ alkenyl (e.g., vinyl, allyl, crotyl, etc.) which may be substituted with a phenyl group and $C_{6-14}$ aralkyl (e.g., benzyl, phenylethyl, naphthylmethyl, etc.) whose phenyl may be substituted with 1 or 2 $C_{1-5}$ alkoxy (e.g., methoxy, ethoxy, propoxy, etc.), and the like. The number of the substituent is preferably 1 to Examples of the substituent in the optionally substituted $C_{1-20}$ alkyl represented by $Y^1$ include the group represented by $Y^2$—X— (wherein each symbol is as defined above) in the general formula (V), halogen, $C_{1-6}$ alkoxy (e.g., methyl, ethyl, propyl, etc.), mono- or di-($C_{1-6}$ alkoxy)phosphoryl (e.g., methoxyphosphoryl, dimethoxyphosphoryl, ethoxyphosphoryl, etc.), phosphono and the like. The number of the substituent is preferably 1 to 3.

$Y^1$ is preferably the group of the formula: $Y^3$—X—$(CH_2)_{n_2}$—, $Y^4$—X—$(CH_2)n_2$— or D— wherein each group is as defined above.

$Y^3$ is preferably (i) $C_{3-7}$ cycloalkyl (e.g., cyclohexyl, etc.), (ii) $C_{6-14}$ aryl (e.g., phenyl, naphthyl, etc.) which may optionally be substituted with straight or branched $C_{1-6}$ alkyl (e.g., methyl, ethyl, propyl, etc.), halogen, methylene-dioxy or the like and optionally form a condensed ring with a 5 to 6 membered aromatic heterocycle containing 1 to 4 nitrogen atoms or (iii) a 5 to 6 membered aromatic heterocyclic group containing 1 to 2 nitrogen atoms and one sulfur atom or 5 to 6 membered aromatic heterocyclic group (e.g., 2-pyridyl, 3-pyridyl, 4-pyridyl, pyrimidinyl, pyrazinyl, pyridazinyl, pyrazolyl, imidazolyl, thiazolyl, isothiazolyl, benzopyranyl, tetrazolyl, thiadiazolyl, etc.) containing 1 to 4 nitrogen atoms each of which may optionally be substituted with straight or branched $C_{1-6}$ alkyl Or the like and optionally form a condensed ring with a benzene ring. $Y^3$ is more preferably (i) phenyl or (ii) a 5 to 6 membered aromatic heterocyclic group containing 1 to 2 nitrogen atoms and one sulfur atom or 5 to 6 membered aromatic heterocyclic group containing 1 to 4 nitrogen atoms each of which may be optionally be substitued with $C_{1-4}$ alkyl.

$Y^4$ is preferably phenyl or straight or branched $C_{1-7}$ alkyl optionally substituted with $C_{1-4}$ alkoxyphenyl or the like.

Examples of the straight or branched $C_{1-7}$ alkyl, $C_{3-7}$ cycloalkyl, $C_{6-14}$ aryl and heterocyclic group represented by $Y^2$ include the same groups as those described above.

Examples of the substituent in the optionally substituted straight or branched $C_{1-7}$ alkyl represented by $Y^2$ include halogen, hydroxy, $C_{1-6}$ alkoxy (e.g., methoxy, ethoxy, propoxy, butoxy, hexyloxy, etc.), optionally esterified carboxyl and the like. The number of the substituent is preferably 1 to 3.

Examples of the substituent in the $C_{3-7}$ cycloalkyl, $C_{6-14}$ aryl and heterocyclic group each of which may be substituted represented by $Y^2$ include halogen; nitro; straight or branched $C_{1-7}$ alkyl (e.g., methyl, ethyl, isopropyl, etc) or $C_{3-7}$ cycloalkyl (cyclopropyl, cyclopentyl, cyclohexyl, etc.) each of which may be substituted with 1 to 3 substituents such as halogen, hydroxy or $C_{1-6}$ alkoxy (e.g., methoxy, ethoxy, propoxy, etc.); hydroxy; straight or branched $C_{1-6}$ alkoxy (e.g., methoxy, ethoxy, isopropoxy, etc.); $C_{4-6}$ cycloalkoxy (e.g., cyclobutoxy, cyclopentyloxy, cyclohexyloxy); $C_{2-6}$ alkenyloxy (e.g., vinyloxy, allyloxy, crotyloxy, etc.); $C_{6-14}$ aralkyloxy (e.g., benzyloxy, phenylethyloxy, naphthylmethyloxy, etc.); $C_{2-7}$ alkanoyloxy (e.g., acetyloxy, propionyloxy, butyryloxy, etc.); $C_{6-14}$ aryloxy (e.g., phenoxy, naphthyloxy, anthryloxy, etc.); thiol; straight or branched $C_{1-6}$ alkylthio (e.g., methylthio, ethylthio, isopropylthio, etc.); $C_{4-7}$ cycloalkylthio (e.g., cyclopentylthio, cyclohexylthio, cycloheptylthio, etc.); $C_{6-14}$ aralkylthio (e.g., benzylthio, phenylethylthio, naphthylmethylthio, etc.); $C_{2-7}$ alkanoylthio (e.g., acetylthio, propionylthio, butyrylthio, etc.) and the like. The number of the substituent is preferably 1 to 4.

Preferable examples of the lower alkanoyl represented by $R^5$ include $C_{1-6}$ alkyl-carbonyl such as acetyl, propionyl, butyryl, isobutyryl, valeryl, pivaloyl, hexanoyl and the like; sulfonic acid acyl having a $C_{1-6}$ hydrocarbon group [e.g., $C_{1-6}$ alkyl (e.g., methyl, ethyl, propyl, hexyl, etc.), phenyl, etc.] and the like. $R^5$ is preferably hydrogen.

Examples of the substituted hydroxy represented by A and A' include that having an appropriate substituent, particulary, substituent used as a protecting group of hydroxy such as alkoxy, alkenyloxy, aralkyloxy, acyloxy, aryloxy or the like. Examples of the alkoxy include straight or branched $C_{1-6}$ alkoxy (.e.g., methoxy, ethoxy, propoxy, isopropoxy, butoxy, isobutoxy, sec-butoxy, tert-butoxy, pentyloxy, isopentyloxy, neopentyloxy, hexyloxy, etc.) and cyclic $C_{4-6}$ alkoxy (e.g., cyclobutoxy, cyclopentyloxy, cyclohexyloxy, etc.). The alkenyloxy is preferably $C_{2-6}$ alkenyloxy (e.g., allyloxy, crotyloxy, 2-pentenyloxy, 3-hexenyloxy, 2-cyclopentenylmethoxy, etc.). The aralkyloxy is preferably $C_{6-19}$ aralkyloxy, more preferably $C_{6-14}$ aryl-$C_{1-4}$ alkyloxy (e.g., benzyloxy, phenethyloxy, etc.). The acyloxy is preferably alkanoyl such as $C_{2-7}$ alkanoyloxy (e.g., acetyloxy, propionyloxy, n-butyryloxy, iso-butyryloxy, hexanoyloxy, etc.). The aryloxy is preferably $C_{6-14}$ aryloxy (e.g., phenoxy, biphenyloxy, etc.). Further, these groups may be substituted with 1 to 3 substituents such as the above halogen, hydroxy, $C_{1-6}$ alkoxy or the like.

Examples of the substituted thiol represented by A, A' and $Z^1$ include that having an appropriate substituent, particulary, substituent used as a protecting group thereof such as alkylthio, aralkylthio, acylthio or the like. The alkylthio is preferably that having straight or branched $C_{1-6}$ alkyl (e.g., methyl, ethyl, isopropyl, etc.) or $C_{4-7}$ cycloalkyl (e.g., cyclopentyl, cyclohexyl, cycloheptyl, etc.). The aralkylthio is preferably that having $C_{7-19}$ aralkyl (e.g., benzyl, naphthylmethyl, anthrylethyl, etc.), more preferably that having $C_{6-14}$ aryl-$C_{1-4}$ alkyl. The acylthio is preferably that having alkanoyl such as $C_{2-7}$ alkanoyl (e.g., acetyl, propionyl, butyryl, etc.). These alkylthio, aralkylthio and acylthio may further be substituted with 1 to 3 substituents such as the above halogen atom, hydroxy, $C_{1-6}$ alkoxy (e.g., methoxy, ethoxy, propoxy, etc.) or the like.

As the substituted carboxyl represented by A, A' and B, there is, for example, esterified or amidated carboxyl.

Examples of the esterified carboxyl include the group of the formula: —COOR$^{11}$ (wherein R$^{11}$ is an ester residue). Examples of the ester residue represented by R$^{11}$ include the optionally substituted hydrocarbon group or optionally substituted heterocyclic group represented by A.

Examples of the amidated carboxyl include the group of the formula: —CON(R$^{12}$)(R$^{13}$)(wherein R$^{12}$ and R$^{13}$ each are hydrogen, an optionally substituted hydrocarbon group or an optionally substituted heterocyclic group). Examples of the optionally substituted hydrocarbon group and optionally substituted heterocyclic group represented by R$^{12}$ or R$^{13}$ include the same groups as those represented by A.

As the cyclic group in the optionally substituted cyclic group represented by $Y^3$ and $Y^9$ there are, for example, aromatic or nonaromatic carbocyclic or heterocyclic groups. Examples of the aromatic carbocyclic group include the same groups as the aryl exemplifying the above hydrocarbon groups represented by A. Examples of the nonaromatic carbocyclic group include $C_{3-7}$ cycloalkyl (e.g., cyclopropyl, cyclobutyl, cyclopentyl, cyclohexyl, cycloheptyl, etc.) and the like. Examples of the aromatic or nonaromatic heterocyclic group include the same heterocyclic groups as those represented by A. Examples of the substituents of these cyclic groups include the same substituents as those of the above optionally substituted aryl exemplifying the optionally substituted hydrocarbon group represented by A. The cyclic group may have the same or different 1 to 4, preferably 1 to 2 substituents on the ring.

Examples of the alkyl and the substituent in the optionally substituted alkyl represented by $Y^4$ and $Y^6$ include the same alkyl or substituents as those in the above hydrocarbon group represented by A.

Examples of the $C_{5-20}$ alkyl represented by $Y^5$ include alkyl having 5 to 20 carbon atoms in the alkyl exemplifying the above hydrocarbon group represented by A.

Examples of the $C_{1-6}$ alkyl represented by $R^9$, $R^{10}$ and $Y^7$ include alkyl having 1 to 6 carbon atoms in the alkyl exemplifying the above hydrocarbon group represented by A.

Examples of the $C_{5-7}$ cycloalkyl represented by $Y^7$ include cycloalkyl having 5 to 7 carbon atoms in the cycloalkyl exemplifying the above hydrocarbon group represented by A.

Examples of the substituent in the optionally substituted phenyl represented by $Y^6$, $R^{10}$ and $Y^7$ include the same substituents as those of the above aryl exemplifying the hydrocarbon group represented by A.

The oxidized sulfur represented by X means sulfonyl or sulfinyl.

Preferable examples of the salts of the 1,1-bisphosphonic acid in the present invention include conventional nontoxic salts such as salts with an inorganic base [e.g., alkaline metal (e.g., sodium, potassium, etc.), alkaline earth metal (e.g., calcium, magnesium, etc.), ammonia], salts with an organic base (e.g., methylamine, ethylamine, propylamine, isopropylamine, butylamine, tert-butylamine, dimethylamine, diethylamine, trimethylamine, triethylamine, pyridine, picoline, dicyclohexylamine, N,N'-dibenzylethylenediamine, etc.), organic acid addition salts (e.g., formic acid salt, acetic acid salt, trifluoroacetic acid salt, maleic acid salt, tartaric acid salt, methanesulfonic acid salt, benzenesulfonic acid salt, toluenesulfonic acid salt, etc.), inorganic acid addition salts (e.g., hydrochloric acid salt, hydrobromic acid salt, sulfuric acid salt, etc.), salts with an amino acid (e.g., glutamic acid, etc.).

The 1,1-bisphosphonic acid compounds, lower alkyl esters thereof and salts thereof used in the present invention can be prepared according to known or per se known methods described in, for example, JP-A 54-37829, U.S. Pat. No. 4,746,654, EP-A-0151072, JP-A 1-258695, EP-A-325482, EP-A-282309, EP-A-282320, EP-A-0337706, Japanese Patent Application Nos. 3-151484, 3-283073 and 3-287984 and the like.

The 1,1-bisphosphonic acid compounds used in the present invention can also be prepared, for example, according to the following methods.

Method A

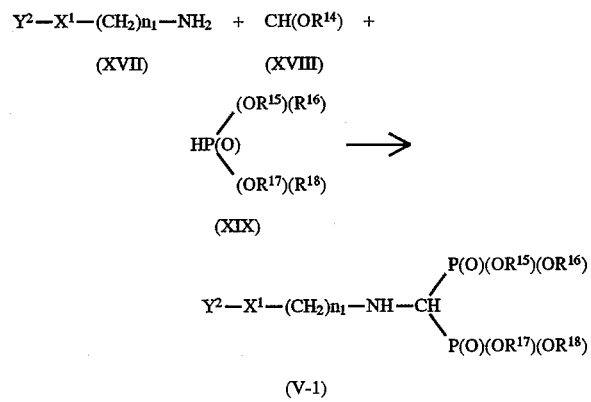

(V-1)

wherein $R^{14}$, $R^{15}$, $R^{16}$, $R^{17}$ and $R^{18}$ are the same or different and are lower alkyl, $X^1$ is an oxygen atom or sulfur atom, and the other symbols are as defined above.

Method B

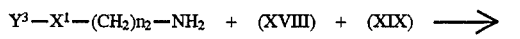

(XX)

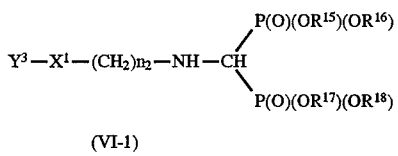

(VI-1)

wherein each symbol is as defined above.

Method C

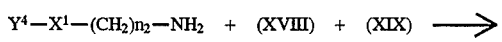

(XXI)

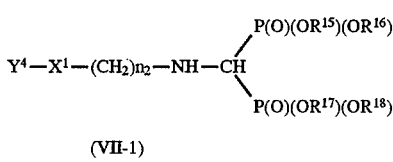

(VII-1)

wherein each symbol is as defined above.

Method D

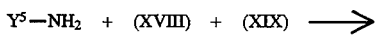

(XXII)

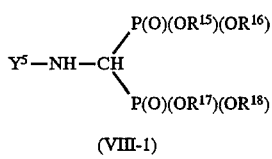

(VIII-1)

wherein each symbol is as defined above.

Examples of the lower alkyl represented by $R^{14}, R^{15}, R^{16}, R^{17}$ and $R^{18}$ in the above formulae include the same lower alkyl as those represented by $R^1$.

In Method A to D above, the amine derivative (XVII), (XX), (XXI) or (XXII) is reacted with the orthoformic acid ester derivative (XVIII) and phosphorous acid ester derivative (XIX) in the corresponding amounts to prepare the bisphosphonic acid ester derivative (V-1), (VI-1), (VII-1) or (VIII-1), respectively. The solvent for the reaction is not specifically required. The reaction is carried out normally at 200° C., preferably 100° C. to 170° C. for 10 minutes to 24 hours.

Method E

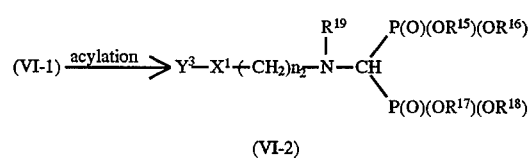

(VI-2)

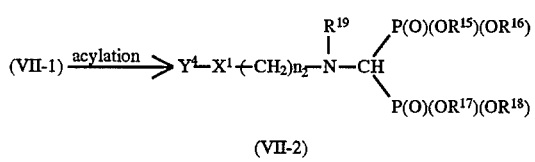

(VII-2)

wherein $R^{19}$ is lower alkanoyl, and the other symbols are as defined above.

Examples of the lower alkanoyl represented by $R^{19}$ in the above formula include the same lower alkanoyl as that represented by $R^5$.

In Method E, the compound (VI-1) or (VII-1) prepared by Method A to D is acylated to prepare the compound (VI-2) or (VII-2). This acylation is carried out by reacting the compound (VI-1) or (VII-1) with 1 to 2 equivalents of an acylating agent (e.g., acid anhydride, acid halide, etc.) in a solvent or in the absence of a solvent. Examples of the solvent include benzene, xylene, toluene, chloroform, dichloromethane, ethyl acetate, ether, tetrahydrofuran and the like. The reaction is carried out at 0° C. to 100° C. for 30 minutes to 10 hours.

Method F

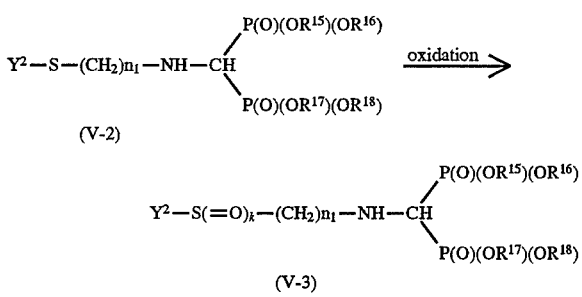

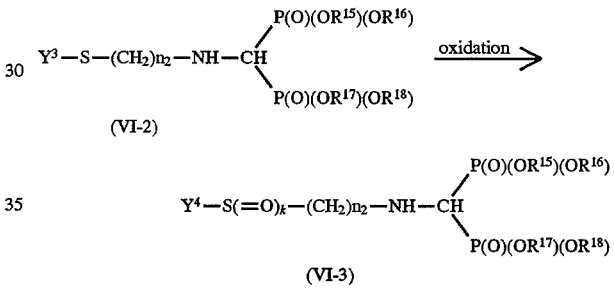

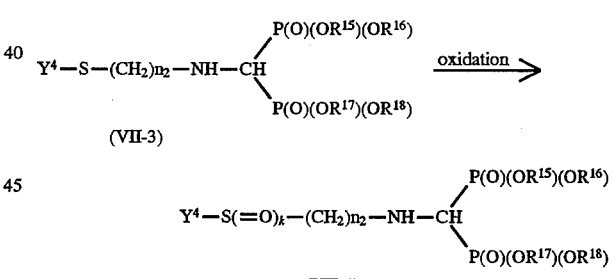

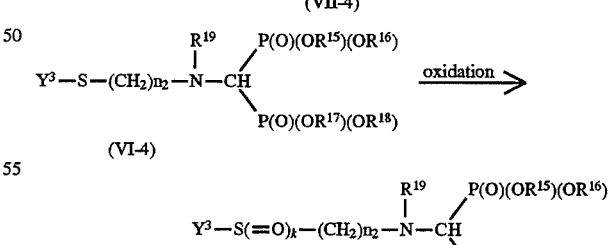

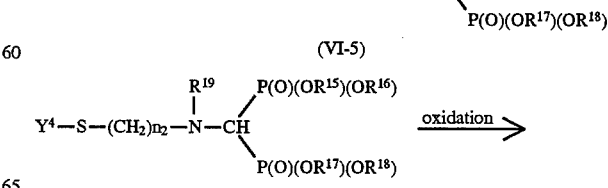

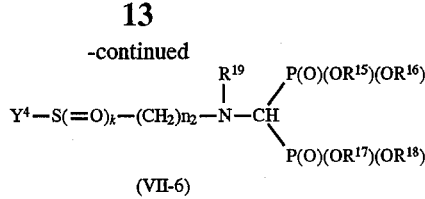

(VII-6)

wherein k is 1 or 2, and the other symbols are as defined above.

The oxidation in Method F is carried out by oxidizing the reactants with an oxidizing agent according to conventional methods.

As the oxidizing agent, there can be used mild oxidizing agents which do not substantially react with the skeleton of sulfur-containing heterocyclic compounds. Preferable examples of them include m-chloroperbenzoic acid, hydrogen peroxide, peresters, sodium metaperiodate and the like.

This reaction is carried out in an orgnic solvent which dose not have a bad influence upon the reaction. Examples of the solvent include halogenated hydrocarbons (e.g., methylene chloride., chloroform, dichloroethane, etc.), hydrocarbons (e.g., benzene, toluene, etc.), alcohols (e.g., methanol, ethanol, propanol etc.), mixed solvents thereof and the like.

When the oxidizing agent is used in an equimolar amount or less based on the compound (V-2), (VI-2), (VII-2), (VI-4) or (VII-5), the compound of the formula (V-3), (VI-3), (VII-4), (VI-5) or (VII-6) wherein k is 1 can be preferentially formed. The compounds of the formulae (V-3), (VI-3), (VII-4), (VI-5) and (VII-6) wherein k is 2 can be formed by further oxidizing the compounds of the formulae (V-3), (VI-3), (VII-4), (VI-5) and (VII-6) wherein k is 1.

This reaction proceeds at room temperature (20° C. to 30° C.) or lower, preferably about −50° C. to 20° C.

Method G

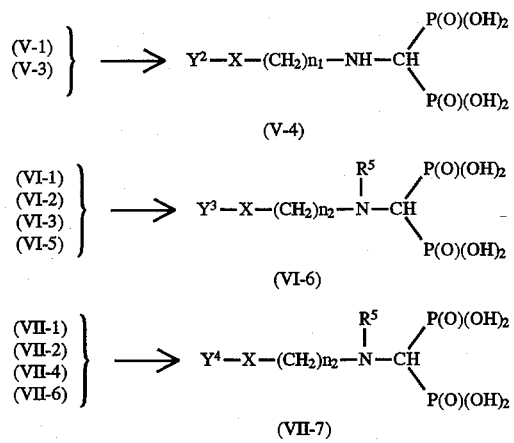

wherein each symbol is as defined above.

In Method G, the bisphosphonic acid esters (V-1), (V-3), (VI-1), (VI-2), (VI-3), (VI-5), (VII-1), (VII-2), (VII-4) and (VII-6) are subjected to hydrolysis to prepare the corresponding bisphosphonic acids.

This reaction is carried out by using inorganic acids (e.g., hydrochloric acid, hydrobromic acid, etc.) or halogenated trialkylsilanes in a solvent which dose not have a bad influence upon the reaction. When the inorganic acids (e.g., hydrochloric acid, hydrobromic acid, etc.) are used, alcohols (e.g., methanol, ethanol, 2-methoxyethanol, ethylene glycol, propanol, butanol, etc.), water or mixed solvents thereof can be used as the solvent. The acid is normally used in large excess. The reaction temperature is 0° C. to 150° C., preferably 30° C. to 100° C. The reaction time is 1 to 50 hours.

When halogenated alkylsilanes (e.g., chlorotrimethylsilane, bromotrimethylsilane, iodotrimethylsilane, etc.) are used, halogenated hydrocarbons (e.g., carbon tetrachloride, chloroform, dichloromethane, 1,2-dichloroethane, 1,1,2,2-tetrachloroethane, etc.), acetonitrile, mixed solvents thereof or the like can be used as the solvent.

The amount of the halogenated alkylsilanes is 4 to 10 equivalents, preferably 5 to 8 equivalents based on the compound (V-1), (V-3), (VI-1), (VI-2), (VI-3), (VI-5), (VII-1), (VII-2), (VII-4) or (VII-6). The reaction temperature is −30° C. to 100° C., preferably −10° C. to 50° C. The reaction time is 30 minutes to 100 hours.

These bisphosphonic acids thus obtained can be converted into their salts according to conventional methods by using a base such as potassium hydroxide, sodium hydroxide, sodium methoxide, ammonia, an organic amine or the like.

Method H

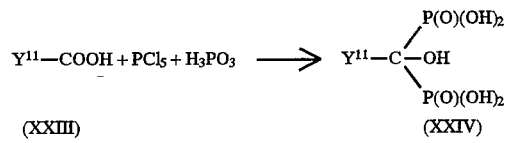

(XXIII)  (XXIV)

wherein $Y^{11}$ is a hydrocarbon group.

Examples of the hydrocarbon group represented by $Y^{11}$ in the above formula include the same hydrocarbon groups as those represented by A.

In Method H, according to conventional methods, for example, the method described in JP-A 56-73091, the carboxylic acid derivative (XXIII) is heated with phosphorus pentachloride and phosphorous acid in chlorobenzene at 30° C. to 150° C., preferably 50° C. to 130° C. for 0.5 to 10 hours, preferably 1 to 5 hours, followed by addition of water and further heating.

Method I

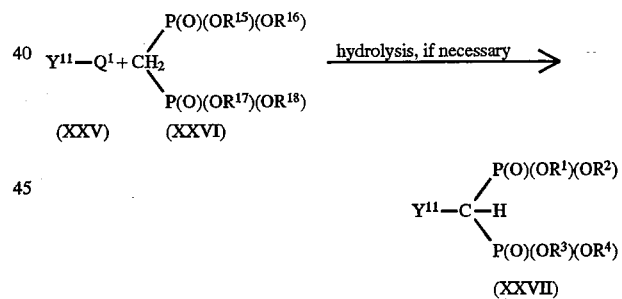

wherein $Q^1$ is a leaving group, and the other symbols are as defined above.

Examples of the leaving group represented by $Q^1$ in the above formula include halogen (preferably chlorine, bromine or iodine), hydroxyl activated by esterification, organic sulfonic acid residues (e.g., p-toluenesulfonyloxy, etc.), $C_{1-4}$ alkylsulfonyloxy (e.g., methanesulfonyloxy, etc.), organic phosphoric acid residues (e.g., diphenylphosphoryloxy, dibenzylphosphoryloxy, dimethylphosphoryloxy, etc.).

In Method I, the compound (XXV) is reacted with the compound (XXVI) in the presence of a base in an appropriate solvent to prepare the compound (XXVII). Examples of the solvent include aromatic hydrocarbons (e.g., benzene, toluene, xylene, etc.), ethers (e.g., dioxane, tetrahydrofuran, dimethoxyethane, etc.), alcohols (e.g., methanol, ethanol, propanol, etc.), ethyl acetate, acetonitrile, pyridine, N,N-dimethylformamide, dimethylsulfoxide, chloroform, dichloromethane, 1,2-dichloroethane, 1,1,2,2-tetrachloroethane, acetone, 2-butanone and mixed solvent thereof. Examples of the base include alkaline metal hydrides (e.g., sodium hydride, potassium hydride, etc.), alkaline metal salts (e.g., sodium hydroxide, potassium hydroxide, etc.), amines (e.g., pyridine, triethylamine, N,N-dimethylaniline, etc.) and the like. The amount of the base to be used is about 1 to 5 mol per 1 mol of the compound (XXVI). This reaction is carried out normally at −20° C. to 150° C., preferably about 0° C. to 130° C. for 1 to 10 hours.

If necessary, the bisphosphonic acid derivative thus obtained is subjected to hydrolysis to convert it into bisphosphonic acid. This hydrolysis can be carried out according to the same manner as in Method G.

Method J

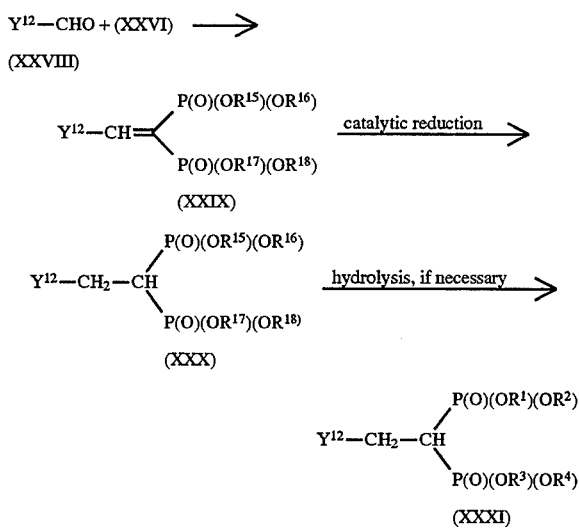

wherein $Y^{12}$ is a hydrocarbon group, and the other symbols are as defined above.

Examples of the hydrocarbon group represented by $Y^{12}$ in the above formula include the same hydrocarbon group as those represented by A.

In Method J, the aldehyde derivative (XXVIII) is condensed with the methylenebisphosphonic acid ester derivative (XXVI) according to the method described in Tetrahedron, 30, 301 (1974). The compound (XXIX) obtained by condensation between the compounds (XXVIII) and (XXVI) is then subjected to catalytic reduction by the method described in the paper to prepare the compound (XXX). The hydrolysis of the compound (XXX) is carried out in the same manner as that in Method G.

The starting material in the present invention can be synthesized according to known or per se known methods described in, for example, EP-A-464509 and EP-A-491374 and the like.

The starting material in the present invention can be synthesized, for example, according to the following method.

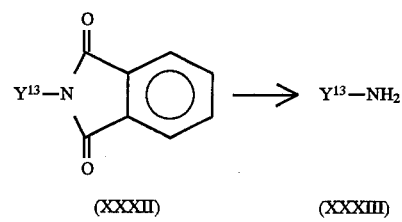

wherein $Y^{13}$ is a hydrocarbon group.

Examples of the hydrocarbon group represented by $Y^{13}$ in the above formula include the same hydrocarbon group as those represented by A.

In this method, the phthalimide derivative (XXXII) is reacted with hydrazine hydrate to prepare the amine derivative (XXXIII). The reaction between the compound (XXXII) and hydrazine hydrate is carried out in an appropriate solvent. Examples of the solvent include aromatic hydrocarbons (e.g., benzene, toluene, xylene, etc.), ethers (e.g., dioxane, tetrahydrofuran, dimethoxyethane, etc.), alcohols (e.g., methanol, ethanol, propanol, etc.), N,N-diemthylformamide, dimethylsulfoxide, chloroform, dichloromethane, 1,2-dichloroethane, 1,1,2,2-tetrachloroethane and mixed solvents thereof. The amount of hydrazine hydrate to be used is 1 to 10 mol, preferably 1.2 to 5 mol per 1 mol of the compound (XXXII). This reaction is carried out normally at −20° C. to 150° C., preferably about 0° C. to 100° C. for 1 to 10 hours.

The compounds used in the present invention can be isolated and purified by known separation and purification methods such as concentration, concentration under reduced pressure, solvent extraction, crystallization, recrystallization, solvent conversion, chromatography and the like.

The compounds used in the present invention has squalene synthetase inhibitory activity. Further, some compounds used in the present invention inhibit an enzyme not present in the biosynthetic pathway of cholesterol. Anyway, since the compounds used in the present invention inhibit biosynthesis of cholesterol, they are useful for prevention and treatment of hypercholesterolemia and coronary arteriosclerosis of mammals (e.g., mouse, rat, rabbit, dog, cat, cattle, pig, human, etc.).

When the compounds in the present invention is administered to humans, the administration may be oral or parenteral. Examples of the composition for the oral administration include solid or liquid preparations such as tablets including sugar coated tablets and film coated tablets, pills, granules, powders, capsules including softcapsules, medicated syrups, emulsions, suspensions and the like. These compositions can be prepared according to per se known methods and they contain carriers and fillers conventionally used in the art. Examples of the carriers and fillers for tablets include lactose, starch, sucrose, magnesium stearate and the like.

As the composition for parenteral administration, there can be used, for example, injections, suppositories and the like. The injections include dosage forms such as subcutaneous injections, intradermal injections, intramuscular injections and the like. The injections can be prepared according to per se known methods, namely, by suspending or emulsifying the compounds used in the present invention in a sterile aqueous or oily solution conventionally used for injections. Examples of the aqueous solution for injections include physiological saline solution, isotonic solution and the like. If necessary, the aqueous solution for injections can be used in combination with an appropriate suspending agent such as carboxymethylcellulose sodium, nonionic detergents or the like. Examples of the oily solution include sesame oil, soybean oil and the like. The oily solution can be used in combination with a solubilizing agent such as benzyl benzoate, benzyl alcohol or the like. The injection solution thus prepared is normally filled into an appropriate ampule.

When the compound used in the present invention is used as a treating agent for hypercholesterolemia, the dose to an adult patient per day is 1 to 500 mg, preferably 10 to 200 mg in the case of oral administration. No toxicity is observed in the dose range.

According to the present invention, there are provided a novel squalene inhibitory composition useful as a treating agent for hypercholesterolemia and novel compounds having squalene synthetase inhibitory activity.

EXAMPLE

The following experiments, test examples, preparations and reference examples further illustrate the present invention in detail, but are not to be construed to limit the scope thereof.

Squalene synthetase inhibitory activity and cholesterol biosynthesis inhibitory activity of the compounds used in the present invention were determined by the following method.

Determination of squalene synthetase inhibitory activity

The squalene synthetase inhibitory activity was determined as follows by using the enzyme solutions shown in Experiments 1 and 2 below.

Each enzyme solution (Protein: 0.8 µg) prepared in Experiments 1 and 2 was added to a solution (total amount: 50 µl) containing 5 µM[1-$^3$H]farnesylpyrophosphoric acid (Specific activity 25 µCi/µmole), 1 mM NADPH, 5 mM MgCl$_2$, 6 mM glutathione, 100 mM potassium phosphate buffer (pH 7.4) and a drug to be tested (which was added as a solution thereof in water or DMSO). The mixture was allowed to react at 37° C. for 45 minutes. A mixture (150 µl) of chloroform and methanol (1:2) was added to stop the reaction. Then, chloroform (50 µl) and 3N sodium hydroxide solution (50 µl) were added. The chloroform layer (under layer, 50 µl) containing the reaction products in which the major component was squalene was mixed with toluene liquid scintillator (3 ml). The radioactivity was measured with a liquid scintillation counter.

The squalene synthetase inhibitory activity is indicated by the concentration (IC$_{50}$, molarity(M)) which inhibits the radioactivity incorporated into the chloroform layer by 50%.

Experiment 1

Preparation of rat enzyme

SD-Male rats (6 weeks old) were bled to death followed by removal of liver. The liver (ca. 10 g) was washed with ice-cooled physiological saline, homogenized in an ice-cooled buffer solution (15 ml) [100 mM potassium phosphate (pH 7.4), 15 mM nicotinamide, 2 mM MgCl$_2$] and centrifuged at 10,000×g for 20 minutes (4° C.). The resulting supernatant was further centrifuged at 105,000×g for 90 minutes (4° C.). Then, the deposit was suspended in an ice-cooled 100 mM potassium phosphate buffer solution (pH 7.4) and centrifuged at 105,000×g for 90 minutes (4° C.) again. The deposit (microsome fraction) thus obtained was suspended in an ice-cooled 100 mM potassium phosphate buffer solution (pH 7.4) so that the protein concentration became about 40 mg/ml (measured with BCA Protein Assay Kit (Pias)), and the suspension was used as the enzyme solution.

Experiment 2

Preparation of human enzyme

Cultivation was carried out on Dulbecco modified Eagle medium containing 10% bovine fetal serum in the presence of 5% CO$_2$ at 37° C. The human hepatoma cells HepG2 (ca. 1×10$^9$ cells) were suspended in an ice-cooled buffer solution (10 ml) [100 mM potassium phosphate (pH 7.4), 30 mM nicotinamide, 2.5 mM MgCl$_2$], and the cells were crushed by ultrasonication (30 seconds, twice). From the resulting sonicate, microsome fraction was obtained according to the same manner as that described in Experiment 1. This microsome fraction was suspended in an ice-cooled 100 mM potassium phosphate buffer solution (pH 7.4) so that the protein concentration became about 4 mg/ml, and this suspension was used as the enzyme liquid.

Determination of cholesterol biosynthesis Inhibitory activity

The liver was excised from Sprague-Dawley rat (6 weeks old, male) under full feeding and sliced into 500 µm in thickness. The slices of liver (150–200 mg) and KHB buffer solution (1 ml) containing 0.5 µCi [2-$^{14}$C] acetic acid and various concentrations of test compounds were incubated at 37° C. for 2 hours. Cholesterol was extracted from the reaction mixture. The amount of cholesterol synthesized from the labeled acetic acid was measured, and the inhibitory ratio was calculated in comparison with the synthesized amount in the case of no addition of the test compounds.

Test Example 1

Squalene synthetase inhibitory activity was determined with regard to Compound Nos. 1 to 20 prepared according to the methods described in Japanese Patent Application Nos. 3-151484, 3-283073 and 3-287984 and EP-A-325482 and Compound No. 21 (Preparation 1). IC$_{50}$ (M) shown in Tables 1, 2 and 3 were obtained.

TABLE 1

$$\text{(A)}-(CH_2)_n-NH-CH\begin{matrix}P(O)(OR)_2\\P(O)(OR)_2\end{matrix}$$

| Cpd No. | (A)— | n | R | Rat enzyme | Human enzyme |
|---|---|---|---|---|---|
| 1 | 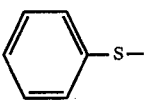 | 4 | H(4Na salt) | 1.8 × 10$^{-8}$ | 8.9 × 10$^{-9}$ |

TABLE 1-continued $$\text{(A)}-(CH_2)_n-NH-CH\begin{matrix}P(O)(OR)_2\\ \\P(O)(OR)_2\end{matrix}$$

| Cpd No. | (A)— | n | R | Rat enzyme | Human enzyme |
|---|---|---|---|---|---|
| 2 | 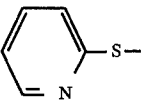 | 4 | H(HCl salt) | $9.7 \times 10^{-8}$ | $1.8 \times 10^{-7}$ |
| 3 | 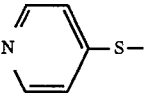 | 4 | H(HCl salt) | $2.1 \times 10^{-7}$ | $3.0 \times 10^{-7}$ |
| 4 | $C_2H_5-S-$ | 4 | H | $3.7 \times 10^{-7}$ | $1.3 \times 10^{-6}$ |
| 5 | $(CH_3)_3C-S-$ | 4 | H(2Na salt) | $7.6 \times 10^{-7}$ | $9.1 \times 10^{-6}$ |
| 6 | 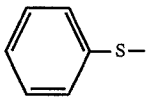 | 5 | H(4Na salt) | $5.7 \times 10^{-9}$ | $2.3 \times 10^{-9}$ |
| 7 | 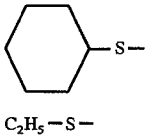 | 5 | H(3Na salt) | $1.9 \times 10^{-8}$ | $1.8 \times 10^{-8}$ |
| 8 | $C_2H_5-S-$ | 5 | H | $6.8 \times 10^{-8}$ | $1.1 \times 10^{-7}$ |
| 9 | 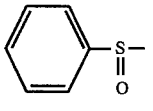 | 4 | H(4Na salt) | $9.0 \times 10^{-9}$ | $6.3 \times 10^{-9}$ |
| 10 | 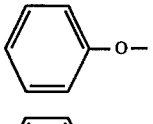 | 5 | H(4Na salt) | $8.1 \times 10^{-9}$ | $5.2 \times 10^{-9}$ |
| 11 | 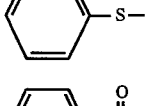 | 6 | H(4Na salt) | $3.6 \times 10^{-9}$ | $1.5 \times 10^{-9}$ |
| 12 | 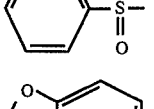 | 4 | H(4Na salt) | $6.4 \times 10^{-6}$ | — |
| 13 | 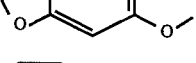 | 4 | H(3Na salt) | $1.9 \times 10^{-8}$ | $1.4 \times 10^{-8}$ |
| 14 | 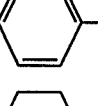 | 5 | $C_2H_5$ | $5.6 \times 10^{-7}$ | $4.5 \times 10^{-7}$ |
| 15 | 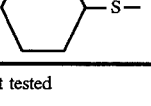 | 5 | $C_2H_5$ | $4.1 \times 10^{-6}$ | — |

—: Not tested

TABLE 2

$$\text{(A)}-(CH_2)_n-NH-CH \begin{matrix} P(O)(OR)_2 \\ P(O)(OR)_2 \end{matrix}$$

| Cpd No. | (A)— | n | R | Rat enzyme | Human enzyme |
|---|---|---|---|---|---|
| 16 | phenyl-(CH$_2$)$_2$—S— | 2 | H(2Na salt) | $2.0 \times 10^{-8}$ | $9.7 \times 10^{-9}$ |
| 17 | phenyl-CH$_2$—S— | 3 | H(2Na salt) | $1.8 \times 10^{-8}$ | $1.2 \times 10^{-8}$ |
| 18 | phenyl-(CH$_2$)$_2$—S— | 2 | C$_2$H$_5$ | $7.9 \times 10^{-7}$ | $6.1 \times 10^{-7}$ |
| 19 | phenyl-S— | 6 | C$_2$H$_5$ | $7.5 \times 10^{-6}$ | $6.9 \times 10^{-6}$ |

TABLE 3

Compound No. 20

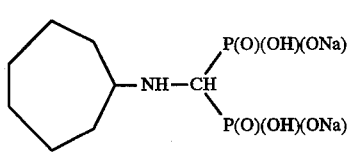

Compound No. 21

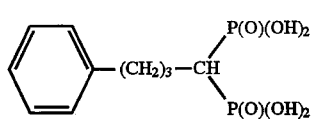

| Cpd No. | Rat enzyme | Human enzyme |
|---|---|---|
| 20 | $9.4 \times 10^{-7}$ | $6.4 \times 10^{-6}$ |
| 21 | $5.5 \times 10^{-6}$ | — |

—: Not tested

Test Example 2

The effect of Compound No. 22 (Example 39 described in Japanese Patent Application No. 3-151484) (added in 20 μM), 67, 74 and 75 on cholesterol synthesis from [2-$^{14}$C] acetic acid in assay using liver slices of rats was observed. As a result, significant inhibition of cholesterol biosynthesis was confirmed as shown in Table 4.

TABLE 4

Compound No. 22

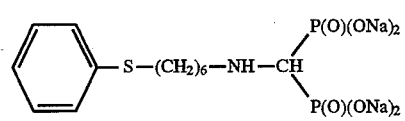

| Cpd No. | Concentration | Activity |
|---|---|---|
| No addition | | $100 \pm 0$ |
| 22 | 20 μM | $52.9 \pm 10.0$ |
| 67 | 20 μM | $43.4 \pm 5.0$ |
| 74 | 20 μM | $35.8 \pm 0.8$ |
| 75 | 20 μM | $50.0 \pm 7.9$ |

Test Example 3

Squalene synthetase inhibitory activity was determined with regard to compounds prepared according to the following Preparation. As a result, IC$_{50}$ shown in Tables 5 to 6 were obtained.

TABLE 5

| Cpd No. | Rat enzyme(M) | Human enzyme(M) |
|---|---|---|
| 28 | $6.2 \times 10^{-6}$ | $3.2 \times 10^{-6}$ |
| 60 | $6.0 \times 10^{-9}$ | $3.1 \times 10^{-9}$ |
| 61 | $5.8 \times 10^{-10}$ | $4.7 \times 10^{-10}$ |
| 63 | $4.3 \times 10^{-9}$ | $2.2 \times 10^{-9}$ |
| 66 | $4.7 \times 10^{-9}$ | $4.0 \times 10^{-9}$ |
| 67 | $8.7 \times 10^{-9}$ | $9.3 \times 10^{-9}$ |
| 72 | $4.5 \times 10^{-9}$ | $4.6 \times 10^{-9}$ |
| 79 | $8.8 \times 10^{-9}$ | $7.0 \times 10^{-9}$ |
| 81 | $2.0 \times 10^{-7}$ | $1.8 \times 10^{-6}$ |
| 83 | $4.3 \times 10^{-9}$ | $8.4 \times 10^{-9}$ |
| 86 | $2.7 \times 10^{-8}$ | $3.5 \times 10^{-8}$ |
| 88 | $1.3 \times 10^{-8}$ | $1.1 \times 10^{-8}$ |
| 89 | $8.1 \times 10^{-9}$ | — |
| 93 | $1.9 \times 10^{-8}$ | $2.0 \times 10^{-8}$ |

TABLE 5-continued

| Cpd No. | Rat enzyme(M) | Human enzyme(M) |
|---|---|---|
| 99 | $6.9 \times 10^{-9}$ | $6.7 \times 10^{-9}$ |
| 100 | $1.2 \times 10^{-8}$ | $1.2 \times 10^{-8}$ |
| 101 | $7.8 \times 10^{-9}$ | $6.1 \times 10^{-9}$ |
| 102 | $3.1 \times 10^{-9}$ | $3.0 \times 10^{-9}$ |
| 106 | $6.2 \times 10^{-8}$ | $1.1 \times 10^{-7}$ |
| 108 | $2.3 \times 10^{-8}$ | $4.4 \times 10^{-8}$ |

TABLE 6

| Cpd No. | Rat enzyme(M) | Human enzyme(M) |
|---|---|---|
| 109 | $1.3 \times 10^{-6}$ | $5.8 \times 10^{-6}$ |
| 110 | $4.4 \times 10^{-8}$ | $6.1 \times 10^{-8}$ |
| 111 | $1.9 \times 10^{-8}$ | $2.2 \times 10^{-8}$ |
| 112 | $3.3 \times 10^{-6}$ | $8.2 \times 10^{-6}$ |
| 113 | $1.5 \times 10^{-8}$ | $9.8 \times 10^{-9}$ |

Preparation 1

Preparation of Compound (Cpd) No. 21

(1) Preparation of tetraisopropyl 2-styrylvinylidenebisphosphonate

A solution of titanium tetrachloride (2.8 g) in carbon tetrachloride (3.5 ml) was added to tetrahydrofuran (30 ml) with stirring under ice cooling. Cinnamaldehyde (1.0 g) and tetraisopropylmethylenediphosphonate (2.6 g) were added to the mixture. The resulting mixture was stirred for 30 minutes under ice cooling. Further, N-methylmorpholine (1.5 g) was added to the mixture and the resulting mixture was stirred overnight at room temperature. The reaction mixture was poured into ice-water and extracted with ethyl acetate. The ethyl acetate layer was washed successively with water and a saturated aqueous solution of sodium bicarbonate and dried ($MgSO_4$). The solvent was distilled off to obtain crystals of tetraisopropyl 2-styrylvinylidenebisphosphonate (1.25 g, 36.0%). The crystals were recrystallized from isopropyl ether-hexane. Colorless prism, mp: 103°–104° C.

Elemental Analysis for $C_{22}H_{36}O_6P_2$: Calcd.: C, 57.64; H, 7.91 Found: C, 57.48; H, 7.64

(2) Preparation of tetraisopropyl 4-phenylbutylidene-1,1-bisphosphonate

A mixture of tetraisopropyl 2-styrylvinylidenebisphosphonate (4.0 g), 5% palladium-carbon (1 g) and ethanol (200 ml) was stirred under a stream of hydrogen for 2 hours. Palladium-carbon was filtered off and the solvent in the filtrate was distilled off. The residual oil was subjected to column chromatography on silica gel. Oily tetraisopropyl 4-phenylbutylidene-1,1-bisphosphonate (2.56 g, 63.7%) was obtained from the fractions obtained by elution with acetone-hexane (1:1, v/v).

NMR (δ ppm, $CDCl_3$): 1.29–1.33 (24H, m), 1.75–2.05 (4H, m), 2.15 (1H, tt, J=24.0,6.0 Hz), 2.63 (2H, t, J=7.2 Hz), 4.67–4.85 (4H, m), 7.13–7.32 (5H, m).

Elemental Analysis for $C_{22}H_{40}O_6P_2$: Calcd.: C, 57.13; H, 8.72 Found: C, 56.83 H, 8.93

(3) Preparation of 4-phenylbutylidene-1,1-bisphosphonic acid

Bromotrimethylsilane (3.0 g) was added to a solution of tetraisopropyl 4-phenylbutylidene-1,1-bisphosphonate (2.0 g) in acetonitrile (7 ml). The mixture was stirred at room temperature for 2 days. The reaction mixture was diluted with water (10 ml). The mixture was stirred at room temperature for 30 minutes and then concentrated to obtain crystals of 4-phenylbutylidene-1,1-bisphosphonic acid (1.0 g, 78.7%). The crystals were recrystallized from water-acetone. Colorless prism, mp: 191°–192° C.

Elemental Analysis for $C_{10}H_{16}O_6P_2$: Calcd.: C, 40.83; H, 5.48 Found: C, 40.57; H, 5.59

Preparation 2

Preparation of Compound No. 23

A mixture of 10-(phenylthio)decylamine (5.78 g), ethyl orthoformate (8.07 g) and diethyl phosphite [$HP(O)(OC_2H_5)_2$](15.03 g) was stirred at 150° C. for 3 hours. The reaction mixture was concentrated under reduced pressure and the residual oil was subjected to column chromatography on silica gel. Tetraethyl 10-(phenylthio)decylaminomethylenebisphosphonate (5.33 g, 44.4%) was obtained as an oil from the fractions obtained by elution with chloroformethyl acetate-methanol (15:15:1, v/v).

NMR (δ ppm in $CDCl_3$): 1.26–1.45 (14H, m), 1.35 (12H, t, J=7 Hz), 1.57–1.68 (3H, m), 2.82 (2H, t, J=7 Hz), 2.92 (2H, t, J=7 Hz), 3.25 (1H, t, J=22 Hz), 4.14–4.30 (8H, m), 7.16–7.36 (5H, m).

Preparations 3 to 28

Preparation of Compound Nos. 24 to 49

According to the same manner as that described in Preparation 2, compounds in Tables 7 to 13 were obtained.

TABLE 7

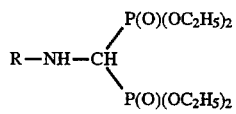

| Cpd No. | R | Yield (%) | NMR (δ ppm, in $CDCl_3$) |
|---|---|---|---|
| 24 |  | 45.9 | 0.84(3H, d, J=5Hz), 0.87(9H, d, J=7Hz), 1.02–1.57(17H, m), 1.35 (12H, t, J=7Hz), 1.74(1H, s), 2.80–2.87(2H, m), 3.25(1H, t, J=22Hz), 4.14–4.30(8H, m). |

TABLE 7-continued

R—NH—CH(P(O)(OC$_2$H$_5$)$_2$)$_2$

| Cpd No. | R | Yield (%) | NMR (δ ppm, in CDCl$_3$) |
|---|---|---|---|
| 25 | C$_6$H$_5$—S—(CH$_2$)$_{12}$— | 28.0 | 1.35(12H, t, J=7Hz), 1.25–1.45 (16H, m), 1.57–1.68(5H, m), 2.82 (2H, t, J=7Hz), 2.91(2H, t, J=7Hz), 3.25(1H, t, J=22Hz), 4.13–4.30 (8H, m), 7.15–7.35(5H, m)$_o$ |
| 26 | (naphthyl)—S—(CH$_2$)$_6$— | 47.7 | 1.34(12H, t, J=7Hz), 1.25–1.54 (6H, m), 1.63–1.74(3H, m), 2.82 (2H, t, J=7Hz), 3.02(2H, t, J=7Hz), 3.24(1H, t, J=22Hz), 4.13–4.29 (8H, m), 7.39–7.51(3H, m), 7.73–7.81(4H, m)$_o$ |
| 27 | CH$_3$O—C$_6$H$_4$—CH$_2$S(CH$_2$)$_6$— | 44.2 | 1.35(12H, t, J=7Hz), 1.20–1.58 (9H, m), 2.39(2H, t, J=7Hz), 2.81 (2H, t, J=7Hz), 3.24(1H, t, J=22Hz), 3.66(2H, S), 3.80(3H, S), 4.14–4.30(8H, m), 6.85(2H, d, J=9Hz), 7.23(2H, d, J=9Hz)$_o$ |
| 28 | Cl—C$_6$H$_4$—S—(CH$_2$)$_6$— | 48.6 | 1.35(12H, t, J=7Hz), 1.25–1.50 (6H, m), 1.55–1.66(3H, m), 2.82 (2H, t, J=7Hz), 2.88(2H, t, J=7Hz), 3.24(1H, t, J=22Hz), 4.14–4.30 (8H, m), 7.25(4H, S)$_o$ |

TABLE 8

R—NH—CH(P(O)(OC$_2$H$_5$)$_2$)$_2$

| Cpd No. | R | Yield (%) | NMR (δ ppm, in CDCl$_3$) |
|---|---|---|---|
| 29 | CH$_3$—C$_6$H$_4$—S—(CH$_2$)$_6$— | 44.2 | 1.34(12H, t, J=7Hz), 1.25–1.64 (9H, m), 2.32(3H, S), 2.81(2H, t, J=7Hz), 2.86(2H, t, J=7Hz), 3.23 (1H, t, J=22Hz), 4.13–4.29(8H, m), 7.09(2H, d, J=8Hz), 7.24(2H, d, J=8Hz)$_o$ |
| 30 | C$_6$H$_5$—S—(CH$_2$)$_{11}$— | 47.5 | 1.13–1.48(16H, m), 1.35(12H, t, J=7Hz), 1.57–1.68(3H, m), 2.82 (2H, t, J=7Hz), 2.92(2H, t, J=7Hz), 3.25(1H, t, J=22Hz), 4.14–4.30 (8H, m), 7.16–7.36(5H, m)$_o$ |
| 31 | (pyrimidin-2-yl)—S—(CH$_2$)$_6$— | 37.5 | 1.34(12H, t, J=7Hz), 1.19–1.54 (6H, m), 1.60–1.76(3H, m), 2.83 (2H, t, J=6Hz), 3.13(2H, t, J=7Hz), 3.24(1H, t, J=22Hz), 4.10–4.30 (8H, m), 6.94(1H, t, J=5Hz), 8.50 (2H, d, J=5Hz)$_o$ |
| 32 | (thiazol-2-yl)—S—(CH$_2$)$_6$— | 45.3 | 1.35(12H, t, J=7Hz), 1.25–1.52 (6H, m), 1.69–1.82(3H, m), 2.83 (2H, t, J=7Hz), 3.20(2H, t, J=7Hz), 3.26(1H, t, J=22Hz), 4.14–4.30 (8H, m), 7.21(1H, d, J=3Hz), 7.66 (1H, d, J=3Hz)$_o$ |

TABLE 9

R—NH—CH(P(O)(OC$_2$H$_5$)$_2$)$_2$

| Cpd No. | R | Yield (%) | NMR (δ ppm, in CDCl$_3$) |
|---|---|---|---|
| 33 | CH$_3$-(thiazole)-S—(CH$_2$)$_6$— | 30.3 | 1.35(12H, t, J=7Hz), 1.25–1.52 (6H, m), 1.71–1.81(3H, m), 2.72 (3H, S), 2.83(2H, t, J=7Hz), 3.25 (1H, t, J=22Hz), 3.29(2H, t, J=7H), 4.14–4.30(8H, m)$_o$ |
| 34 | (N-methylimidazole)-S—(CH$_2$)$_6$— | 31.0 | 1.34(12H, t, J=7Hz), 1.21–1.48 (6H, m), 1.58–1.72(3H, m), 2.81 (2H, t, J=7Hz), 3.05(2H, t, J=7Hz), 3.23(1H, t, J=22Hz), 3.61(3H, S), 4.10–4.29(8H, m), 6.91(1H, d, J=1Hz), 7.05(1H, d, J=1Hz)$_o$ |
| 35 | (N-methyltriazole)-S—(CH$_2$)$_6$— | 41.8 | 1.35(12H, t, J=7Hz), 1.19–1.51 (6H, m), 1.73–1.84(3H, m), 2.83 (2H, t, J=6Hz), 3.24(1H, t, J=22Hz), 3.34(2H, t, J=7Hz), 3.91 (3H, S), 4.10–4.29(8H, m)$_o$ |
| 36 | (pyrimidine)-S—(CH$_2$)$_7$— | 39.6 | 1.35(12H, t, J=7Hz), 1.32–1.45 (8H, m), 1.66–1.80(3H, m), 2.82 (2H, t, J=7Hz), 3.13(2H, t, J=7Hz), 3.25(1H, t, J=22Hz), 4.13–4.30 (8H, m), 6.94(1H, t, J=5Hz), 8.50 (2H, d, J=5Hz)$_o$ |

TABLE 10

R—NH—CH(P(O)(OC$_2$H$_5$)$_2$)$_2$

| Cpd No. | R | Yield (%) | NMR (δ ppm, in CDCl$_3$) |
|---|---|---|---|
| 37 | (pyrimidine)-S—(CH$_2$)$_8$— | 37.9 | 1.35(12H, t, J=7Hz), 1.22–1.48 (10H, m), 1.63–1.80(3H, m), 2.82 (2H, t, J=7Hz), 3.14(2H, t, J=7Hz), 3.25(1H, t, J=22Hz), 4.14–4.30 (8H, m), 6.95(1H, t, J=5Hz), 8.51 (2H, d, J=5Hz)$_o$ |
| 38 | (pyrimidine)-S—(CH$_2$)$_9$— | 45.9 | 1.35(12H, t, J=7Hz), 1.25–1.48 (12H, m), 1.64–1.77(3H, m), 2.81 (2H, t, J=7Hz), 3.14(2H, t, J=7Hz), 3.24(1H, t, J=22Hz), 4.13–4.30 (8H, m), 6.94(1H, t, J=5Hz), 8.50 (2H, d, J=5Hz)$_o$ |
| 39 | (pyrimidine)-S—(CH$_2$)$_{10}$— | 36.5 | 1.35(12H, t, J=7Hz), 1.27–1.48 (14H, m), 1.66–1.77(3H, m), 2.82 (2H, t, J=7Hz), 3.14(2H, t, J=7Hz), 3.25(1H, t, J=22Hz), 4.13–4.30 (8H, m), 6.94(1H, t, J=5Hz), 8.50 (2H, d, J=5Hz)$_o$ |

TABLE 10-continued

R—NH—CH(P(O)(OC$_2$H$_5$)$_2$)(P(O)(OC$_2$H$_5$)$_2$)

| Cpd No. | R | Yield (%) | NMR (δ ppm, in CDCl$_3$) |
|---|---|---|---|
| 40 | pyridine-fused pyrazole–S—(CH$_2$)$_6$— | 13.1 | 1.35(12H, t, J=7Hz), 1.23–1.48 (6H, m), 1.64–1.75(3H, m), 2.81 (2H, t, J=7Hz), 3.15(2H, t, J=7Hz), 3.23(1H, t, J=22Hz), 4.11–4.29 (8H, m), 6.93(1H, t, J=7Hz), 7.30 (1H, ddd, J=1&7&9Hz), 7.78(1H, dt, J=9&1Hz), 8.12(1H, dt, J=7& 1Hz). |

TABLE 11

R—NH—CH(P(O)(OC$_2$H$_5$)$_2$)(P(O)(OC$_2$H$_5$)$_2$)

| Cpd No. | R | Yield (%) | NMR (δ ppm, in CDCl$_3$) |
|---|---|---|---|
| 41 | imidazo[1,2-a]pyridine–S—(CH$_2$)$_6$— | 25.4 | 1.34(12H, t, J=7Hz), 1.22–1.46 (6H, m), 1.60–1.71(3H, m), 2.83 (2H, t, J=6Hz), 2.99(2H, t, J=7Hz), 3.24(1H, t, J=22Hz), 4.11–4.29 (8H, m), 6.89(1H, t, J=7Hz), 7.17 (1H, dd, J=7&9Hz), 7.58(1H, d, J= 9Hz), 7.70(1H, d, J=1Hz), 7.83 (1H, s). |
| 42 | benzothiazol-2-yl–S—(CH$_2$)$_6$— | 42.4 | 1.34(12H, t, J=7Hz), 1.19–1.56 (6H, m), 1.72–1.85(3H, m), 2.83 (2H, t, J=6Hz), 3.24(1H, t, J= 22Hz), 3.34(2H, t, J=7Hz), 4.10– 4.29(8H, m), 7.28(1H, dt, J=1& 8Hz), 7.41(1H, dt, J=1&8Hz), 7.75 (1H, dd, J=1&8Hz), 7.86(1H, dd, J= 1&8Hz). |
| 43 | phenyl–S—(CH$_2$)$_8$— | 49.2 | 1.35(12H, t, J=7Hz), 1.26–1.48 (8H, m), 1.60–1.71(5H, m), 2.81 (2H, t, J=7Hz), 2.91(2H, t, J=7Hz), 3.25(1H, t, J=22Hz), 4.14–4.28 (8H, m), 7.16–7.35(5H, m). |
| 44 | phenyl–S—(CH$_2$)$_9$— | 53.6 | 1.35(12H, t, J=7Hz), 1.27–1.48 (11H, m), 1.57–1.68(4H, m), 2.81 (2H, t, J=7Hz), 2.91(2H, t, J=7Hz), 3.25(1H, t, J=22Hz), 4.14–4.30 (8H, m), 7.16–7.35(5H, m). |

TABLE 12

$$R-NH-CH\begin{matrix}P(O)(OC_2H_5)_2\\P(O)(OC_2H_5)_2\end{matrix}$$

| Cpd No. | R | Yield (%) | NMR (δ ppm, in CDCl$_3$) |
|---|---|---|---|
| 45 | CH$_3$\C(CH$_3$)=CH-CH$_2$-CH$_2$-C(CH$_3$)=CH-CH$_2$- | 24.1 | 1.35(12H, t, J=7Hz), 1.60(6H, S), 1.65(3H, S), 1.69(3H, S), 1.71(1H, S), 2.01–2.07(4H, m), 3.31(1H, t, J=22Hz), 3.47(2H, d, J=7Hz), 4.11–4.31(8H, m), 5.06–5.10(1H, m), 5.21(1H, dt, J=1&7Hz)ₒ |
| 46 | C$_6$H$_5$-S-(CH$_2$)$_7$- | 36.3 | 1.35(12H, t, J=7Hz), 1.26–1.45 (7H, m), 1.57–1.65(4H, m), 2.81 (2H, t, J=7Hz), 2.91(2H, t, J=7Hz), 3.24(1H, t, J=22Hz), 4.13–4.30 (8H, m), 7.15–7.34(5H, m)ₒ |
| 47 | CH$_3$\C(CH$_3$)=CH-CH$_2$-CH$_2$-C(CH$_3$)=CH-CH$_2$-CH$_2$-C(CH$_3$)=CH-CH$_2$- | 32.1 | 1.35(12H, t, J=7Hz), 1.60(6H, S), 1.66(3H, S), 1.68(4H, S), 1.94–2.10(8H, m), 3.30(1H, t, J=22Hz), 3.47(2H, d, J=7Hz), 4.11–4.30(8H, m), 5.06–5.10(2H, m), 5.21(1H, dt, J=1&7Hz)ₒ |
| 48 | C$_6$H$_5$-N(COCH$_3$)-(CH$_2$)$_4$- | 54.3 | 1.33(12H, t, J=7Hz), 1.40–1.90 (4H, m), 1.82(3H, S), 2.81(2H, t, J=7Hz), 3.21(1H, t, J=22Hz), 3.70 (2H, t, J=7Hz), 4.10–4.30(8H, m), 7.12–7.20(2H, m), 7.33–7.48(3H, m)ₒ |

TABLE 13

$$R-NH-CH\begin{matrix}P(O)(OC_2H_5)_2\\P(O)(OC_2H_5)_2\end{matrix}$$

| Cpd No. | R | Yield (%) | NMR (δ ppm, in CDCl$_3$) |
|---|---|---|---|
| 49 | C$_6$H$_5$-(CH$_2$)$_5$- | 30.7 | 1.34(3H, t, J=7Hz), 1.43–1.66(7H, m), 2.60(2H, t, J=8Hz), 2.83(2H, t, J=7Hz), 3.24(1H, t, J=22Hz), 4.13–4.29(8H, m), 7.14–7.19(3H, m), 7.23–7.31(2H, m)ₒ |

Preparation 29

Preparation of Compound No. 50 m-Chloroperbenzoic acid (2.62 g) in limited amounts was added to a solution of tetraethyl 6-(phenylthio) hexylaminomethylenebisphosphonate (6.85 g) in dichloromethane (100 ml) under ice-cooling over 30 minutes. The reaction mixture was stirred under ice-cooling for 3 hours, and then washed with a saturated aqueous solution of sodium bicarbonate and water and dried (MgSO$_4$). The solvent was distilled off under reduced pressure. The residual oil was subjected to column chromatography on silica gel. Tetraethyl 6-(phenylsulfinyl) hexylaminomethylenebisphosphonate (5.84 g, 82.6%) was obtained as an oil from the fractions obtained by elution with ethyl acetate-chloroform-methanol (10:10:1, v/v).

NMR (δ ppm in CDCl$_3$): 1.21–1.45 (5H, m), 1.34 (12H, t, J=7 Hz), 1.61–1.80 (4H, m), 2.78 (2H, t, J=7 Hz), 2.81 (2H, t, J=7 Hz), 3.23 (1H, t, J=22 Hz), 4.13–4.29 (8H, m), 7.50–7.56 (3H, m), 7.58–7.65 (2H, m).

Preparations 30 to 38

Preparation of Compound Nos. 51 to 59

According to the same manner as that described in Preparation 29, the compounds in Tables 14 to 15 were obtained.

TABLE 14

R—NH—CH(P(O)(OC₂H₅)₂)(P(O)(OC₂H₅)₂)

| Cpd No. | R | Yield (%) | NMR (δ ppm, in CDCl₃) |
|---|---|---|---|
| 51 | phenyl-S(=O)-(CH₂)₁₀— | 77.2 | 1.35(12H, t, J=7Hz), 1.25–1.77 (17H, m), 2.78(2H, t, J=8Hz), 2.82 (2H, t, J=7Hz), 3.25(1H, t, J=22Hz), 4.11–4.30(8H, m), 7.49–7.56(3H, m), 7.58–7.66(2H, m)ₒ |
| 52 | phenyl-S(=O)-(CH₂)₁₂— | 81.5 | 1.24–1.76(21H, m), 1.35(12H, t, J=7Hz), 2.78(2H, t, J=8Hz), 2.82 (2H, t, J=6Hz), 3.25(1H, t, J=22Hz), 4.10–4.30(8H, m), 7.48–7.55(3H, m), 7.57–7.65(2H, m)ₒ |
| 53 | 2-naphthyl-S(=O)-(CH₂)₆— | 88.5 | 1.33(12H, t, J=7Hz), 1.24–1.84 (9H, m), 2.80(2H, t, J=6Hz), 2.87 (2H, t, J=8Hz), 3.22(1H, t, J=22Hz), 4.11–4.28(8H, m), 7.56–7.64(3H, m), 7.90–8.01(3H, m), 8.19(1H, S)ₒ |
| 54 | 4-Cl-phenyl-S(=O)-(CH₂)₆— | 84.1 | 1.34(12H, t, J=7Hz), 1.22–1.76 (9H, m), 2.76(2H, t, J=8Hz), 2.81 (2H, t, J=7Hz), 3.22(1H, t, J=22Hz), 4.13–4.29(8H, m), 7.50(2H, d, J=9Hz), 7.57)2H, d, J=9Hz)ₒ |
| 55 | 4-CH₃-phenyl-S(=O)-(CH₂)₆— | 83.3 | 1.34(12H, t, J=7Hz), 1.22–1.73 (9H, m), 2.42(3H, S), 2.76(2H, t, J=8Hz), 2.80(2H, t, J=7Hz), 3.22 (1H, t, J=22Hz), 4.13–4.29(8H, m), 7.32(2H, d, J=8Hz), 7.50(2H, d, J=8Hz)ₒ |

TABLE 15

R—NH—CH(P(O)(OC₂H₂))(P(O)(OC₂H₅)₂)

| Cpd No. | R | Yield (%) | NMR (δ ppm, in CDCl₃) |
|---|---|---|---|
| 56 | phenyl-S(=O)-(CH₂)₁₁— | 81.3 | 1.35(12H, t, J=7Hz), 1.12–1.76 (19H, m), 2.78(2H, t, J=7Hz), 2.81 (2H, t, J=7Hz), 3.24(1H, t, J=22Hz), 4.13–4.30(8H, m), 7.49–7.55 (3H, m), 7.57–7.65 (2H, m)ₒ |
| 57 | phenyl-S(=O)-(CH₂)₇— | 85.9 | 1.35(12H, t, J=7Hz), 1.25–1.82 (11H, m), 2.78(2H, t, J=8Hz), 2.81 (2H, t, J=6Hz), 3.24(1H, t, J=22Hz), 4.14–4.30(8H, m), 7.50–7.58(3H, m), 7.61–7.66(2H, m)ₒ |

TABLE 15-continued $$R-NH-CH \begin{matrix} P(O)(OC_2H_2) \\ P(O)(OC_2H_5)_2 \end{matrix}$$

| Cpd No. | R | Yield (%) | NMR (δ ppm, in CDCl$_3$) |
|---|---|---|---|
| 58 | 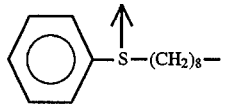 | 80.9 | 1.35(12H, t, J=7Hz), 1.19–1.76 (13H, m), 2.78(2H, t, J=7Hz), 2.81 (2H, t, J=7Hz), 3.24(1H, t, J= 22Hz), 4.13–4.29(8H, m), 7.50– 7.55(3H, m), 7.57–7.65(2H, m)$_o$ |
| 59 | 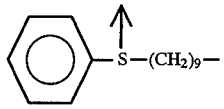 | 82.1 | 1.35(12H, t, J=7Hz), 1.22–1.47 (11H, m), 1.61–1.75(4H, m), 2.78 (2H, t, J=7Hz), 2.81(2H, t, J=7Hz), 3.24(1H, t, J=22Hz), 4.10–4.30 (8H, m), 7.49–7.55(3H, m), 7.58– 7.65(2H, m)$_o$ |

Preparation 39

Preparation of Compound No. 60

Bromotrimethylsilane (3.05 g) was added to a solution of tetraethyl 6-(phenylsulfinyl)hexylaminomethylenebisphosphonate (1.7 g) in acetonitrile (25 ml). The mixture was stirred at room temperature for 15 hours. Water (0.79 ml) was added to the reaction mixture, which was then stirred at room temperature for 1 hour. The deposited solid was separated by filtration. The solid was suspended in methanol (15 ml). A solution (28%, 2.11 g) of sodium methoxide in methanol was added to the suspension, followed by addition of water (2 ml) and ether (45 ml). After stirring at room temperature for 1 hour, the deposited crystals were separated by filtration. The resulting crystals were recrystallized from water-methanol to obtain disodium 6-(phenylsulfinyl) hexylaminomethylenebisphosphonate (0.57 g, 36%). Colorless prism. mp: higher than 300° C.

Elemental Analysis for $C_{13}H_{21}NO_7SP_2Na_2 \cdot 3/2H_2O$: Calcd.: C, 33.20; H, 5.14; N, 2.98 Found: C, 33.45; H, 4.93; N, 3.01

Preparations 40 to 67

Preparation of Compound Nos. 61 to 88

According to the same manner as that described in Preparation 39, compounds in Tables 16 to 19 were obtained.

TABLE 16

$$R-NH-CH \begin{matrix} P(O)(OH)(ONa) \\ P(O)(OH)(ONa) \end{matrix}$$

| Cpd No. | R | Yield (%) | mp (°C.) | Recrystn solvent | Molecular formula |
|---|---|---|---|---|---|
| 61 | 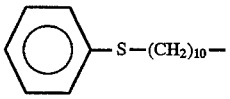 | 35.0 | >300 | water-methanol | $C_{17}H_{29}NO_6SP_2Na_2$ .3/2H$_2$O |
| 62 | 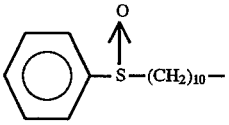 | 40.0 | >300 | water-methanol | $C_{17}H_{29}NO_7SP_2Na_2$ .H$_2$O |
| 63 | CH$_3$–CH(CH$_3$)–CH$_2$–CH$_2$–CH(CH$_3$)–CH$_2$–CH$_2$–CH(CH$_3$)–CH$_2$– | 33.0 | >300 | water-methanol | $C_{16}H_{35}NO_6P_2Na_2$ .2H$_2$O |
| 64 | 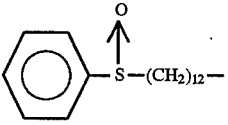 | 24.0 | >300 | water-methanol | $C_{19}H_{33}NO_7SP_2Na_2$ .3/2H$_2$O |

TABLE 16-continued $$R-NH-CH\begin{array}{c}P(O)(OH)(ONa)\\P(O)(OH)(ONa)\end{array}$$

| Cpd No. | R | Yield (%) | mp (°C.) | Recrystn solvent | Molecular formula |
|---|---|---|---|---|---|
| 65 | naphthyl-S—(CH$_2$)$_6$— | 68.3 | >300 | water-methanol | C$_{17}$H$_{23}$NO$_6$SP$_2$Na$_2$ .3/2H$_2$O |
| 66 | naphthyl-S(O)—(CH$_2$)$_6$— | 56.1 | >300 | water-methanol | C$_{17}$H$_{23}$NO$_7$SP$_2$Na$_2$ .3/2H$_2$O |
| 67 | CH$_3$O—C$_6$H$_4$—CH$_2$—S—(CH$_2$)$_6$— | 48.0 | >300 | water-methanol | C$_{15}$H$_{25}$NO$_7$SP$_2$Na$_2$ .H$_2$O |
| 68 | Cl—C$_6$H$_4$—S—(CH$_2$)$_6$— | 59.0 | >300 | water-methanol | C$_{13}$H$_{20}$NO$_6$SP$_2$ClNa$_2$ .3/2H$_2$O |
| 69 | Cl—C$_6$H$_4$—S(O)—(CH$_2$)$_6$— | 38.0 | >300 | water-methanol | C$_{13}$H$_{20}$NO$_7$SP$_2$ClNa$_2$ .1/2H$_2$O |

TABLE 17

$$R-NH-CH\begin{array}{c}P(O)(OH)(ONa)\\P(O)(OH)(ONa)\end{array}$$

| Cpd No. | R | Yield (%) | mp (°C.) | Recrystn solvent | Molecular formula |
|---|---|---|---|---|---|
| 70 | CH$_3$—C$_6$H$_4$—S—(CH$_2$)$_6$— | 64.0 | >300 | water-methanol | C$_{14}$H$_{23}$NO$_6$SP$_2$Na$_2$ .3/2H$_2$O |
| 71 | CH$_3$—C$_6$H$_4$—S(O)—(CH$_2$)$_6$— | 19.0 | >300 | water-methanol | C$_{14}$H$_{23}$NO$_7$SP$_2$Na$_2$ .H$_2$O |
| 72 | C$_6$H$_5$—S(O)—(CH$_2$)$_{11}$— | 38.0 | >300 | water-methanol | C$_{18}$H$_{31}$NO$_7$SP$_2$Na$_2$ .H$_2$O |

TABLE 17-continued $$R-NH-CH\begin{matrix}P(O)(OH)(ONa)\\ \\P(O)(OH)(ONa)\end{matrix}$$

| Cpd No. | R | Yield (%) | mp (°C.) | Recrystn solvent | Molecular formula |
|---|---|---|---|---|---|
| 73 | pyrazine-S-(CH$_2$)$_6$- | 36.0 | >300 | water-methanol | C$_{11}$H$_{19}$N$_3$O$_6$SP$_2$Na$_2$ · 1/2H$_2$O |
| 74 | thiazole-S-(CH$_2$)$_6$- | 13.0 | >300 | water-methanol | C$_{10}$H$_{18}$N$_2$O$_6$S$_2$P$_2$Na$_2$ · H$_2$O |
| 75 | 5-methyl-1,3,4-thiadiazole-S-(CH$_2$)$_6$- (CH$_3$ substituted) | 46.0 | >300 | water-methanol | C$_{10}$H$_{19}$N$_3$O$_6$SP$_2$Na$_2$ · 1/2H$_2$O |
| 76 | 1-methylimidazole-S-(CH$_2$)$_6$- | 57.8 | >300 | water-methanol-ether | C$_{11}$H$_{21}$N$_3$O$_6$SP$_2$Na$_2$ · 3/2H$_2$O |
| 77 | pyrazine-S-(CH$_2$)$_7$- | 37.4 | >300 | water-methanol | C$_{12}$H$_{21}$N$_3$O$_6$SP$_2$Na$_2$ · 2H$_2$O |
| 78 | pyrazine-S-(CH$_2$)$_8$- | 54.1 | >300 | water-methanol | C$_{13}$H$_{23}$N$_3$O$_6$SP$_2$Na$_2$ · 5/2H$_2$O |

TABLE 18

$$R-NH-CH\begin{matrix}P(O)(OH)(ONa)\\ \\P(O)(OH)(ONa)\end{matrix}$$

| Cpd No. | R | Yield (%) | mp (°C.) | Recrystn solvent | Molecular formula |
|---|---|---|---|---|---|
| 79 | pyrazine-S-(CH$_2$)$_9$- | 36.3 | >300 | water-methanol | C$_{14}$H$_{25}$N$_3$O$_6$SP$_2$Na$_2$ · 2H$_2$O |
| 80 | pyrazine-S-(CH$_2$)$_{10}$- | 50.3 | >300 | water-methanol | C$_{15}$H$_{27}$N$_3$O$_6$SP$_2$Na$_2$ · 2H$_2$O |
| 81 | pyridyl-pyrazole-S-(CH$_2$)$_6$- | 43.0 | >300 | water-methanol | C$_{13}$H$_{20}$N$_4$O$_6$SP$_2$Na$_2$ · 1/2H$_2$O |

TABLE 18-continued $$R-NH-CH\begin{matrix}P(O)(OH)(ONa)\\P(O)(OH)(ONa)\end{matrix}$$

| Cpd No. | R | Yield (%) | mp (°C.) | Recrystn solvent | Molecular formula |
|---|---|---|---|---|---|
| 82 | 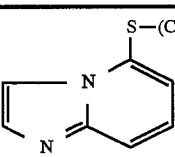 | 16.0 | >300 | water-methanol | $C_{14}H_{21}N_3O_6SP_2Na_2$ .2$H_2O$ |
| 83 | 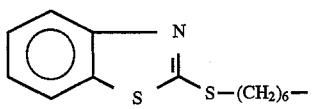 | 61.5 | >300 | water-methanol | $C_{14}H_{20}N_2O_6S_2P_2Na_2$ .3/2$H_2O$ |
| 84 | 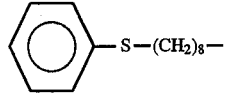 | 43.0 | >300 | water-methanol | $C_{15}H_{25}NO_6SP_2Na_2$ .1/2$H_2O$ |
| 85 | 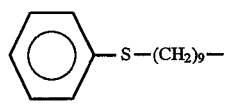 | 41.0 | >300 | water-methanol | $C_{16}H_{27}NO_6SP_2Na_2$ .1/2$H_2O$ |
| 86 | 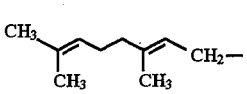 | 35.0 | >300 | water-methanol | $C_{11}H_{21}NO_6P_2Na_2$ .1/2$H_2O$ |
| 87 | 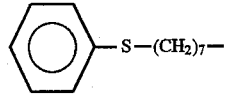 | 52.1 | >300 | water-methanol | $C_{14}H_{23}NO_6SP_2Na_2$ .1/2$H_2O$ |

TABLE 19

$$R-NH-CH\begin{matrix}P(O)(OH)(ONa)\\P(O)(OH)(ONa)\end{matrix}$$

| Cpd No. | R | Yield (%) | mp (°C.) | Recrystn solvent | Molecular formula |
|---|---|---|---|---|---|
| 88 | 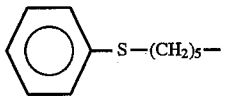 | 53.9 | >300 | water-methanol | $C_{12}H_{19}NO_6P_2Na_2$ .5/2$H_2O$ |

Preparation 68

Preparation of Compound No. 89

Bromotrimethylsilane (1.87 g) was added to a solution of tetraethyl 12-(phenylthio)dodecylaminomethylenebisphosphonate (1.18 g) in acetonitrile (15 ml), and the mixture was stirred at room temperature for 15 hours. Water (0.5 ml) was added to the reaction mixture, which was then stirred at room temperature for 1 hour and concentrated under reduced pressure. The residue was dissolved in methanol-ether (1:3, 40 ml). A solution (28%, 1.57 g) of sodium methoxide in methanol and water (4 ml) were added, and the deposited crystals were separated by filtration. The crystals were recrystallized from water-methanol to obtain monosodium 12-(phenylthio)dodecylaminomethylenebisphosphonate (0.49 g, 48%). Colorless prism, mp: higher than 300° C.

Elemental Analysis for $C_{19}H_{34}NO_6SP_2Na.1/2H_2O$: Calcd.: C, 45.78; H, 7.08; N, 2.81 Found: C, 46.00; H, 7.01; N, 2.73

Preparations 69 to 72

Preparation of Compound Nos. 90 to 93

According to the same manner as that described in Preparation 68, the compounds in Table 20 were obtained.

TABLE 20

$$R-NH-CH\begin{matrix}P(O)(OH)_2\\P(O)(OH)(ONa)\end{matrix}$$

| Cpd No. | R | Yield (%) | mp (°C.) | Recrystn solvent | Molecular formula |
|---|---|---|---|---|---|
| 90 | Ph-S(=O)-(CH$_2$)$_7$— | 52.0 | >300 | water-methanol | $C_{14}H_{24}NO_7SP_2Na \cdot H_2O$ |
| 91 | Ph-S(=O)-(CH$_2$)$_8$— | 34.0 | >300 | water-methanol | $C_{15}H_{26}NO_7SP_2Na \cdot H_2O$ |
| 92 | Ph-S(=O)-(CH$_2$)$_9$— | 30.0 | >300 | water-methanol | $C_{16}H_{28}NO_7SP_2Na \cdot 3/2H_2O$ |
| 93 | (CH$_3$)$_2$C=CH-CH$_2$-CH$_2$-C(CH$_3$)=CH-CH$_2$-CH$_2$-C(CH$_3$)=CH-CH$_2$— | 21.0 | >300 | water-methanol | $C_{16}H_{30}NO_6P_2Na \cdot 3/2H_2O$ |

Preparation 73

Preparation of Compound No. 94

A mixture of disodium 4-phenoxybutylaminomethylenebisphosphonate monohydrate (2.01 g) and concentrated hydrochloric acid (12 ml) was stirred at room temperature for 1 hour. The deposited crystals were separated by filtration. The crystals were added to a mixture of water (50 ml) and tris(hydroxymethyl)aminomethane (0.95 g). The reaction mixture was subjected to lyophilization to obtain 4-phenoxybutylaminomethyl- enebisphosphonic acid di[tris (hydroxymethyl)aminomethane] salt (2.22 g, 76.2%) as colorless powder. mp: 98°–100° C.

Elemental Analysis for $C_{19}H_{41}N_3O_{13}P_2$: Calcd.: C, 39.25; H, 7.11; N, 7.23 Found: C, 39.17; H, 7.25; N, 7.25

Preparation 74

Preparation of Compound No. 95

Bromotrimethylsilane (2.60 g) was added to a solution of tetraethyl 6-(phenylthio)hexylaminomethylenebisphosphonate (1.4 g) in acetonitrile (20 ml), and the mixture was stirred at room temperature for 15 hours. Water (0.7 ml) was added to the reaction mixture, which was then stirred at room temperature for 1 hour. The deposited solid was separated by filtration. The solid was added to a mixture of water (45 ml) and tris(hydroxymethyl)aminomethane (0.46 g). The reaction mixture was subjected to lyophilization to obtain 6-(phenylthio)hexylaminomethylenebisphosphonic acid di[tris(hydroxymethyl)aminomethane] salt (1.15 g, 64.1%) as colorless powder. mp: 92°–94° C.

Elemental Analysis for $C_{21}H_{45}N_3O_{12}SP_2 \cdot 1/2H_2O$: Calcd.: C, 39.75; H, 7.31; N, 6.62 Found: C, 39.93; H, 7.39; N, 6.47

Preparations 75 to 80

Preparation of Compound Nos. 96 to 101

According to the same manner as that described in Preparation 74, the compounds in Table 21 were obtained.

TABLE 21

$$R-NH-CH\begin{matrix}P(O)(OH)_2\\P(O)(OH)_2\end{matrix} \cdot \left(HOCH_2-\underset{CH_2OH}{\underset{|}{\overset{CH_2OH}{\overset{|}{C}}}}-NH_2\right)_2$$

| Cpd No. | R | Yield (%) | mp (°C.) | Molecular formula |
|---|---|---|---|---|
| 96 | Ph—S—(CH$_2$)$_9$— | 69.9 | 103–105 | $C_{24}H_{51}N_3O_{12}SP_2 \cdot 1/2H_2O$ |

TABLE 21-continued $$R-NH-CH\begin{matrix}P(O)(OH)_2\\\\P(O)(OH)_2\end{matrix} \cdot \left(HOCH_2-\overset{\overset{\displaystyle CH_2OH}{|}}{\underset{\underset{\displaystyle CH_2OH}{|}}{C}}-NH_2\right)_2$$

| Cpd No. | R | Yield (%) | mp (°C.) | Molecular formula |
|---|---|---|---|---|
| 97 | 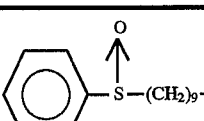 | 71.0 | 104–106 | $C_{24}H_{51}N_3O_{13}SP_2$ |
| 98 | 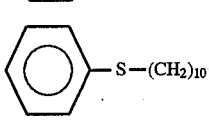 | 46.0 | 87–89 | $C_{25}H_{53}N_3O_{12}SP_2$ |
| 99 | 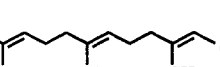 | 55.0 | 93–95 | $C_{24}H_{53}N_3O_{12}P_2$ .3H$_2$O |
| 100 | 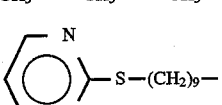 | 59.9 | 94–96 | $C_{22}H_{49}N_5O_{12}SP_2$ .3/2H$_2$O |
| 101 | 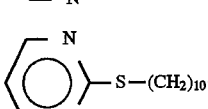 | 64.2 | 99–101 | $C_{23}H_{51}N_5O_{12}SP_2$ .H$_2$O |

Preparation 81

Preparation of Compound No. 102

Bromotrimethylsilane (3.90 g) was added to a solution of tetraethyl 11-(phenylthio)undecylaminomethylenebisphosphonate (2.40 g) in acetonitrile (35 ml), and the mixture was stirred at room temperature for 15 hours. Water (1.0 ml) was added to the reaction mixture, which was then stirred at room temperature for 1 hour and concentrated under reduced pressure. The residue was dissolved in methanol-ether (1:3, 80 ml). A solution of sodium methoxide in methanol (28%, 3.34 g) and water (4 ml) were added. The deposited crystals were separated by filtration. The crystals were recrystallized from water-methanol to obtain trisodium 11-(phenylthio)undecylaminomethylenebisphosphonate (1.33 g, 59.3%). Colorless prism, mp: higher than 300° C.

Elemental Analysis for $C_{18}H_{30}NO_6SP_2Na_3 \cdot 1/2H_2O$: Calcd.: C, 40.91; H, 5.91; N, 2.65 Found: C, 40.85; H, 6.14; N, 2.54

Preparation 82

Preparation of Compound No. 103

According to the same manner as that described in Preparation 81, trisodium 6-(1-methyl-1,2,3,4-tetrazol-5-ylthio)hexylaminomethylenebisphosphonate was obtained. Colorless prism, mp: higher than 300° C.

Elemental Analysis for $C_9H_{18}N_5O_6SP_2Na_3 \cdot H_2O$: Calcd.: C, 22.84; H, 4.26; N, 14.80 Found: C, 23.09; H, 4.25; N, 14.65

Preparation 83

Preparation of Compound No. 104

Oily sodium hydride (60%, 0.24 g) was added to a solution of tetraisopropyl methylenebisphosphonate (3.44 g) in dimethoxyethane (25 ml). The mixture was stirred at room temperature for 1 hour. Then, a solution of (E,E)-farnesyl bromide (1.43 g) in dimethoxyethane (5 ml) was added dropwise at 0° C. The reaction mixture was stirred at room temperature for 1 hour, then poured into water and extracted with ethyl acetate. The organic layer was washed with water and dried (MgSO$_4$), and then the solvent was distilled off under reduced pressure. The oily residue was subjected to column chromatography on silica gel. Tetraisopropyl (E,E)-farnesylmethylenebisphosphonate (1.67 g, 60.9%) was obtained as an oil from the fractions obtained by elution with ethyl acetate-chloroform (1:1, v/v).

NMR (δ ppm in CDCl$_3$): 1.34 (18H, d, J=6 Hz), 1.35 (6H, d, J=6 Hz), 1.60 (6H, s), 1.64 (3H, s), 1.68 (3H, s), 1.95–2.08 (8H, m), 2.17 (1H, tt, J=6&24 Hz), 2.6 (1H, tt, J=7&17 Hz), 4.78 (4H, sextet, J=6 Hz), 5.06–5.14 (2H, m), 5.35 (1H, t, J=7 Hz).

Preparation 84

Preparation of Compound No. 105

According to the same manner as that described in Preparation 83, tetraisopropyl (E)-geranylmethylenebisphosphonate (52.1%) was obtained as an oil.

NMR (δ ppm in CDCl$_3$): 1.34 (18H, d, J=6 Hz), 1.35 (6H, d, J=6 Hz), 1.60 (3H, s), 1.64 (3H, s), 1.68 (3H, d, J=1 Hz), 1.93–2.13 (4H, m), 2.17 (1H, tt, J=6&24 Hz), 2.60 (1H, tt, J=7&17 Hz), 4.78 (4H, sextet, J=6 Hz), 5.05–5.13 (1H, m), 5.35 (1H, t, J=7 Hz).

Preparation 85

Preparation of Compound No. 106

Bromotrimethylsilane (5.02 g) was added to a solution of tetraisopropyl (E,E)-farnesylmethylenebisphosphonate (3.0 g) in acetonitrile (40 ml). The mixture was stirred at room temperature for 15 hours. Water (1.3 ml) was added to the reaction mixture. The mixture was stirred at room temperature for 1 hour and concentrated under reduced pressure. The residue was dissolved in methanol-ether (1:3, 60 ml), and a solution (28%, 4.22 g) of sodium methoxide in methanol and water (2 ml) were added. The deposited crystals were separated by filtration. The crystals were recrystallized from water-methanol to obtain trisodium (E,E)-farnesylmethylenebisphosphonate (0.09 g, 3.0%). Colorless prism, mp: higher than 300° C.

Elemental Analysis for $C_{16}H_{27}O_6P_2Na_3.5/2H_2O$: Calcd.: C, 39.11; H, 6.56 Found: C, 39.04; H, 6.42

Preparation 86

Preparation of Compound No. 107

Platinum dioxide ($PtO_2$) (0.1 g) was added to a solution of tetraisopropyl (E,E)-farnesylmethylenebisphosphonate (5.86 g) in ethanol (50 ml)-acetic acid (13 ml). Catalytic reduction was carried out at room temperature and 1 atm. The catalyst was filtered off. The filtrate was poured into water, and the mixture was extracted with ethyl acetate. The ethyl acetate layer was washed with a saturated aqueous solution of sodium bicarbonate and water and dried ($MgSO_4$). The solvent was distilled off to obtain tetraisopropyl 4,8,12-trimethyltridecylidene-1,1-bisphosphonate (5.58 g, 94.3%) as an oil.

Elemental Analysis for $C_{28}H_{60}O_6P_2$: Calcd.: C, 60.63; H, 10.90 Found: C, 60.53; H, 10.82

Preparation 87

Preparation of Compound No. 108

Bromotrimethylsilane (4.97 g) was added to a solution of tetraisopropyl 4,8,12-trimethyltridecylidene-1,1-bisphosphonate (3.0 g) in acetonitrile (40 ml). The mixture was stirred at room temperature for 15 hours. Water (1.3 ml) was added to the reaction mixture. The resulting mixture was stirred at room temperature for 1 hour and then concentrated under reduced pressure. The residue was dissolved in methanol-ether (1:3, 60 ml). A solution (28%, 4.17 g) of sodium methoxide in methanol and water (2 ml) were added. The deposited crystals were separated by filtration. The crystals were recrystallized from water-methanol to obtain disodium 4,8,12-trimethyltridecylidene-1,1-bisphosphonate (1.41 g, 58.1%). Colorless prism, mp: higher than 300° C.

Elemental Analysis for $C_{16}H_{34}O_6P_2Na_2.H_2O$: Calcd.: C, 42.86; H, 8.09 Found: C, 43.00; H, 8.04

Preparation 88

Preparation of Compound No. 109

Phosphorous acid ($H_3PO_3$) (4.0 g) was added to a mixture of phosphorus pentachloride (10.16 g) and chlorobenzene (15 ml). The resulting mixture was stirred at room temperature for 10 minutes. Then 6-(2-pyridylthio)capronic acid (7.33 g) was added, and the mixture was stirred at 110° C. for 3 hours. The chlorobenzene layer was removed, and water (20 ml) was added to the residual syrup. The mixture was heated under reflux for 1 hour and concentrated under reduced pressure. The residue was treated with acetone-ethanol to obtain colorless crystals (1.08 g). The crystals were suspended in methanol (8 ml). A solution (28%, 4.19 g) of sodium methoxide in methanol was added followed by addition of water (0.5 ml) and ether (20 ml). The mixture was stirred at room temperature for 1 hour. The deposited crystals were separated by filtration. The crystals were recrystallized from water-methanol to obtain trisodium 1-hydroxy-6-(2-pyridylthio)hexane-1,1-bisphosphonate (1.52 g, 10.7%). Colorless prism, mp: higher than 300° C.

Elemental Analysis for $C_{11}H_{16}NO_7SP_2Na_3$: Calcd.: C, 30.22; H, 3.69; N, 3.20 Found: C, 29.92; H, 3.99; N, 3.39

Preparation 89

Preparation of Compound No. 110

A mixture of tetraethyl 4-(N-acetyl-N-phenyl)butylaminomethylene-1,1-bisphosphonate (2.0 g) and concentrated hydrochloric acid (50 ml) was heated under reflux for 10 hours. The reaction mixture was concentrated under reduced pressure. The residue was treated with acetone-ethanol to obtain colorless powder. The powder was recrystallized from ethanol-acetone to obtain 4-(phenylamino)butylaminomethylene-1,1-bisphosphonic acid hydrochloride (1.0 g, 61.0 %), mp: 187°–189° C.

Elemental Analysis for $C_{11}H_{20}N_2O_6P_2.HCl.1/2(CH_3)_2CO$: Calcd.: C, 37.19; H, 5.99; N, 6.94 Found: C, 37.51; H, 6.29; N, 7.00

Preparation 90

Preparation of Compound No. 111

Bromotrimethylsilane (2.26 g) was added to a solution of tetraethyl (E,E)-farnesylaminomethylenebisphosphonate (2.50 g) in acetonitrile (25 ml). The mixture was stirred at room temperature for 3 days. Water (0.7 ml) was added to the reaction mixture, and the mixture was stirred at room temperature for 1 hour. The deposited solid was separated by filtration. The solid was suspended in methanol (15 ml). A solution (28%, 0.50 g) of sodium methoxide in methanol was added followed by addition of water (2 ml) and ether (45 ml). The mixture was stirred at room temperature for 1 hour. Then the deposited crystals were separated by filtration. The crystals were recrystallized from water-methanol to obtain (E,E)-farnesylaminomethylenebisphosphonic acid monoethyl ester monosodium salt (0.32 g, 14%). Colorless prism, mp: 188°–189° C.

Elemental Analysis for $C_{18}H_{34}NO_6P_2Na.H_2O$: Calcd.: C, 46.65; H, 7.83; N, 3.02 Found: C, 47.04; H, 7.91; N, 3.12

Preparation 91

Preparation of Compound No. 112

A solution of tetraethyl (E,E)-farnesylaminomethylenebisphosphonate (2.42 g) in ethanol (25 ml) was added to a solution of sodium hydroxide (0.40 g) in ethanol (25 ml). The mixture was stirred under reflux for 4 hours. The reaction mixture was concentrated under reduced pressure. The residue was dissolved in water (5.0 ml). The solution was subjected to ion-exchange chromatography [Amberlite CG-50 ($H^+$-type)] to obtain (E,E)-farnesylaminomethylenebisphosphonic acid diethyl ester disodium salt (0.75 g, 29%). Colorless powder, mp: 116°–118° C. Elemental Analysis for $C_{20}H_{37}NO_6P_2Na_2.5/2H_2O$: Calcd.: C, 44.45; H, 7.83; N, 2.59 Found: C, 44.08; H, 7.60; N, 2.59

Preparation 92

Preparation of Compound No. 113

According to the same manner as that described in Preparation 90, 6-(phenylthio)hexylaminomethylenebisphosphonic acid monoethyl ester monosodium salt was obtained. Colorless prism, mp: 282°–284° C.

Elemental Analysis for $C_{15}H_{26}NO_6SP_2Na.H_2O$: Calcd.: C, 39.91; H, 6.25; N, 3.10 Found: C, 39.57; H, 6.13; N, 3.27

Preparation 93

Preparation of Compound No. 114

According to the same manner as that described in Preparation 91, 6-(phenylthio)hexylaminomethylenebisphosphonic acid diethyl ester monosodium salt was obtained. Colorless powder, mp: 125°–127° C.

Elemental Analysis for $C_{17}H_{30}NO_6SP_2Na$: Calcd.: C, 44.25; H, 6.55; N, 3.04 Found: C, 44.11; H, 6.73; N, 3.27

Reference Example 1

Potassium carbonate (14.55 g) was added to a solution of thiophenol (9.67 g) and 1,10-dibromodecane (26.33 g) in N,N-dimethylformamide (120 ml). The mixture was stirred at room temperature for 3 hours. Then potassium phthalimide (16.25 g) was added to the resulting mixture, and the mixture was stirred at 100° C. for 3 hours. The reaction mixture was poured into water and extracted with ethyl acetate. The ethyl acetate layer was washed with water and dried (MgSO$_4$), and then the solvent was distilled off under reduced pressure. The residual oil was subjected to column chromatography on silica gel and eluted with ethyl acetate-hexane (1:3, v/v) to obtain N-[(10-phenylthio)decyl]phthalimide (10.31 g, 29.7%), which was then recrystallized from isopropyl ether-hexane. Colorless needle, mp: 61°–62° C.

Reference Examples 2 to 6

According to the same manner as that described in Reference Example 1, compounds in Table 22 were obtained.

TABLE 22

| Ref. ex. No. | A– | n | Yield (%) | mp (°C.) | Recrystn solvent |
|---|---|---|---|---|---|
| 2 |  | 12 | 35.0 | 64–65 | isopropyl ether-hexane |
| 3 |  | 11 | 37.0 | 63–64 | ethanol |
| 4 |  | 8 | 30.2 | 70–71 | isopropyl ether-hexane |
| 5 |  | 9 | 37.2 | 67–68 | isopropyl ether-hexane |
| 6 | | 7 | 37.7 | 64–65 | isopropyl ether-hexane |

Reference Example 7

Potassium carbonate (9.95 g) was added to a solution of 2-mercaptopyrimidine (6.73 g) and 1,7-dibromoheptane (15.48 g) in N,N-dimethylformamide (85 ml). The mixture was stirred at room temperature for 3 hours. The reaction mixture was poured into water and extracted with ethyl acetate. The ethyl acetate layer was washed with water and dried (MgSO$_4$), and then the solvent was distilled off under reduced pressure. The residual oil was subjected to column chromatography on silica gel and eluted with ethyl acetate-hexane (1:4, v/v) to obtain 2-(7-bromoheptylthio)pyrimidine (8.5 g) as an oil. This oil was dissolved in N,N-dimethylformamide (45 ml). Potassium phthalimide (5.44 g) was added to the solution, and the mixture was stirred at 100° C. for 3 hours. The reaction mixture was poured into water and extracted with ethyl acetate. The ethyl acetate layer was washed with water and dried (MgSO$_4$). The solvent was distilled off under reduced pressure to obtain N-[7-(2-pyrimidinylthio)heptyl]phthalimide (10.36 g, 48.6%) as an oil.

NMR (δ ppm in CDCl$_3$): 1.33–1.49 (6H, m), 1.61–1.76 (4H, m), 3.13 (2H, t, J=7 Hz), 3.68 (2H, t, J=7 Hz), 6.93 (1H, t, J=5 Hz), 7.68–7.74 (2H, m), 7.79–7.86 (2H, m), 8.49 (2H, d, J=5 Hz).

Reference Example 8

According to the same manner as that described in Reference Example 7, N-[8-(2-pyrimidinylthio)octyl]phthalimide was obtained as an oil. Yield: 48.1%

NMR (δ ppm in CDCl$_3$): 1.26–1.51 (8H, m), 1.59–1.79 (4H, m), 3.13 (2H, t, J=7 Hz), 3.68 (2H, t, J=7 Hz), 6.94 (1H, t, J=5 Hz), 7.69–7.75 (2H, m), 7.80–7.87 (2H, m), 8.51 (2H, d, J=5 Hz).

Reference Example 9

According to the same manner as that described in Reference Example 7, N-[9-(2-pyrimidinylthio)nonyl]phthalimide was obtained as an oil. Yield: 46.5%.

NMR (δ ppm in CDCl$_3$): 1.23–1.47 (10H, m), 1.60–1.79 (4H, m), 3.13 (2H, t, J=7 Hz), 3.68 (2H, t, J=7 Hz), 6.94 (1H, t, J=5 Hz), 7.69–7.75 (2H, m), 7.81–7.87 (2H, m), 8.51 (2H, d, J=5 Hz).

Reference Example 10

According to the same manner as that described in Reference Example 7, N-[10-(2-pyrimidinylthio)decyl]phthalimide was obtained as an oil. Yield: 46.8%.

NMR (δ ppm in CDCl$_3$): 1.19–1.47 (12H, m), 1.61–1.79 (4H, m), 3.14 (2H, t, J=7 Hz), 3.68 (2H, t, J=7 Hz), 6.94 (1H, t, J=5 Hz), 7.69–7.75 (2H, m), 7.81–7.87 (2H, m), 8.51 (2H, d, J=5 Hz).

Reference Example 11

Potassium carbonate (8.29 g) was added to a solution of 2-naphthalenethiol (8.01 g) and 1-bromo-6-chlorohexane (9.98 g) in N,N-dimethylformamide (65 ml). The mixture was stirred at room temperature for 3 hours. Then potassium phthalimide (9.26 g) was added to the mixture, and the resulting mixture was stirred at 100° C. for 3 hours. The reaction mixture was poured into water and extracted with ethyl acetate. The ethyl acetate layer was washed with water and dried (MgSO$_4$), and the solvent was distilled off under reduced pressure to obtain N-[6-(2-naphthylthio)hexyl]phthalimide (18.56 g, 95.3%), which was then recrystallized from ethyl acetate-hexane. Colorless plate, mp: 109°–110° C.

Reference Examples 12 to 19

According to the same manner as that described in Reference Example 11, compounds in Table 23 were obtained.

TABLE 23

A—S—(CH₂)ₙ—N(phthalimide)

| Ref. ex. No. | A— | n | Yield (%) | mp (°C.) | Recrystn solvent |
|---|---|---|---|---|---|
| 12 | CH₃O–C₆H₄–CH₂– | 6 | 51.3 | 49–50 | isopropyl ether-hexane |
| 13 | Cl–C₆H₄– | 6 | 90.7 | 91–92 | ethanol |
| 14 | CH₃–C₆H₄– | 6 | 91.0 | 84–85 | ethanol |
| 15 | pyrimidin-2-yl | 6 | 95.1 | 59–60 | ethanol-hexane |
| 16 | 5-methyl-1,3,4-thiadiazol-2-yl | 6 | 96.5 | 71–72 | ethanol-hexane |
| 17 | 1-methyl-1H-tetrazol-5-yl | 6 | 96.7 | 83–84 | ethanol-hexane |
| 18 | [1,2,4]triazolo[4,3-a]pyridin-3-yl | 6 | 88.3 | 95–96 | ethanol-hexane |
| 19 | benzothiazol-2-yl | 6 | 93.7 | 112–113 | ethanol-hexane |

Reference Example 20

According to the same manner as that described in Reference Example 11, N-[6-(2-thizolylthio)hexyl]phthalimide was obtained as an oil. Yield: 90.5%.

NMR (δ ppm in CDCl₃): 1.33–1.58 (4H, m), 1.62–1.83 (4H, m), 3.20 (2H, t, J=7 Hz), 3.68 (2H, t, J=7 Hz), 7.20 (1H, t, J=3 Hz), 7.66 (1H, d, J=3 Hz), 7.69–7.75 (2H, m), 7.80–7.87 (2H, m).

Reference Example 21

According to the same manner as that described in Reference Example 11, N-[6-(1-methyl-2-imidazolylthio)hexyl]phthalimide was obtained as an oil. Yield: 90.7%.

NMR (δ ppm in CDCl₃): 1.30–1.50 (4H, m), 1.67(4H, m), 3.06 (2H, t, J=7 Hz), 3.61 (3H, s), 3.67 (2H, t, J=7 Hz), 6.92 (1H, d, J=1 Hz), 7.05 (1H, d, J=1 Hz), 7.69–7.75 (2H, m), 7.80–7.87 (2H, m).

Reference Example 22

According to the same manner as that described in Reference Example 11, N-[6-(imidazolo[1,2-a]pyridin-5-ylthio)hexyl]phthalimide was obtained as an oil. Yield: 61.5%.

NMR (δ ppm in CDCl₃): 1.31–1.57 (4H, m), 1.68 (4H, m), 2.99 (2H, t, J=7 Hz), 3.68 (2H, t, J=7 Hz), 6.88 (1H, d, J=7 Hz), 7.16 (1H, dd, J=7&9 Hz), 7.57 (1H, d, J=9 Hz), 7.69 (1H, s), 7.69–7.76 (2H, m), 7.82 (1H, s), 7.80–7.87 (2H, m).

Reference Example 23

Oily sodium hydride (60%, 2.45 g) was added to a solution of acetanilide (7.0 g) in N,N-diemthylformamide (50 ml), and the mixture was stirred at 0° C. for 15 minutes. Then a solution of N-(4-bromobutyl)phthalimide (15.3 g) in N,N-dimethylformamide (80 ml) was added dropwise. The mixture was stirred at room temperature for 4 hours, poured into water and extracted with ethyl acetate. The ethyl acetate layer was washed with water and dried (MgSO$_4$), and then the solvent was distilled off. The residue was subjected to column chromatography on silica gel and eluted with ethyl acetate-chloroform (1:9, v/v) to obtain N-[4-(N-acetyl-N-phenylamino)butyl]phthalimide (9.21 g, 52.9%), which was then recrystallized from isopropyl ether. Colorless prism, mp: 83°–84° C.

Reference Example 24

A mixture of N-[(10-phenylthio)decyl]phthalimide 10.1 g), hydrazine monohydrate (2.56 g) and ethanol (75 ml) was heated under reflux for 1 hour. The deposited crystals were separated by filtration, and the filtrate was concentrated under reduced pressure. The residual oil was subjected to distillation under reduced pressure to obtain 10-phenylthiodecylamine (5.78 g, 85.3%) as an oil, bp: 174°–176° C. (0.8 mmHg).

Reference Examples 25 to 43

According to the same manner as that described in Reference Example 24, compounds in Tables 24 to 25 were obtained.

TABLE 24

R—NH$_2$

| Ref. ex. No. | R | Yield (%) | bp (°C./mmHg) |
|---|---|---|---|
| 25 | CH$_3$CH(CH$_3$)CH$_2$CH$_2$CH(CH$_3$)CH$_2$CH$_2$CH$_2$CH(CH$_3$)CH$_2$— | 89.9 | 103–106/0.55 |
| 26 | C$_6$H$_5$—S—(CH$_2$)$_{12}$— | 83.0 | mp 86–87° C. (isopropyl ether-hexane) |
| 27 | 2-naphthyl-S—(CH$_2$)$_6$— | 44.9 | 196–198/1.5 |
| 28 | CH$_3$O—C$_6$H$_4$—CH$_2$S(CH$_2$)$_6$— | 75.4 | 166–169/0.55 |
| 29 | Cl—C$_6$H$_4$—S—(CH$_2$)$_6$— | 79.0 | 138–141/0.17 |
| 30 | CH$_3$—C$_6$H$_4$—S—(CH$_2$)$_6$— | 82.0 | 131–134/0.18 |
| 31 | C$_6$H$_5$—S—(CH$_2$)$_{11}$— | 75.5 | 168–171/0.2 |
| 32 | (pyrimidin-2-yl)—S—(CH$_2$)$_6$— | 71.5 | 138–141/0.3 |
| 33 | (thiazol-2-yl)—S—(CH$_2$)$_6$— | 80.4 | 127–129/0.23 |
| 34 | CH$_3$-(1,3,4-thiadiazol-2,5-diyl)—S—(CH$_2$)$_6$— | 54.8 | 149–151/0.35 |

TABLE 24-continued

R—NH₂

| Ref. ex. No. | R | Yield (%) | bp (°C./mmHg) |
|---|---|---|---|
| 35 | 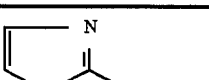 | 78.0 | 154–157/1.0 |
| 36 | 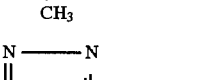 | 46.1 | 170–172/0.4 |

TABLE 25

R—NH₂

| Ref. ex. No. | R | Yield (%) | bp (°C./mmHg) |
|---|---|---|---|
| 37 | pyrazine—S—(CH₂)₇— | 79.1 | 150–152/0.35 |
| 38 | pyrazine—S—(CH₂)₈— | 80.9 | 166–168/0.6 |
| 39 | pyrazine—S—(CH₂)₉— | 81.2 | 169–171/0.4 |
| 40 | pyrazine—S—(CH₂)₁₀— | 80.7 | 175–177/0.35 |
| 41 | phenyl—S—(CH₂)₈— | 82.1 | 155–157/0.8 |
| 42 | phenyl—S—(CH₂)₉— | 46.0 | 161–164/0.6 |
| 43 | phenyl—S—(CH₂)₇— | 80.5 | 138–140/0.30 |

Reference Example 44

A mixture of N-[6-(s-triazolo[4,3-a]pyridin-3-ylthio)hexyl]phthalimide (16.5 g), hydrazine monohydrate (4.34 g) and ethanol (135 ml) was heated under reflux for 1 hour. The deposited crystals were separated by filtration, and the filtrate was concentrated under reduced pressure to obtain 6-(s-triazolo[4,3-a]pyridin-3-ylthio)hexylamine as an oil. Yield: 87.5%.

NMR (δ ppm in CDCl₃): 1.23–1.58 (6H, m), 1.48 (2H, s), 1.72 (2H, m), 2.67 (2H, t, J=7 Hz), 3.15 (2H, t, J=7 Hz), 6.92 (1H, t, J=7 Hz), 7.30 (1H, ddd, J=1&7&9 Hz), 7.77 (1H, d, J=10 Hz), 8.12 (1H, d, J=7 Hz).

Reference Example 45

According to the same manner as that described in Reference Example 44, 6-(imidazolo[1,2-a]pyridin-5-ylthio)hexylamine was obtained as an oil. Yield: 95.9%.

NMR (δ ppm in CDCl₃): 1.24–1.53 (6H, m), 1.39 (2H, s), 1.59–1.75 (2H, m), 2.68 (2H, t, J=7 Hz), 3.00 (2H, t, J=7 Hz), 6.87 (1H, dd, J=1&7 Hz), 7.15 (1H, dd, J=7&9 Hz), 7.56 (1H, d, J=9 Hz), 7.69 (1H, d, J=1 Hz), 7.83 (1H, s).

Reference Example 46

According to the same manner as that described in Reference Example 44, 6-(2-benzothiazolylthio)hexylamine was obtained as an oil. Yield: 78.3%.

NMR (δ ppm in CDCl₃): 1.27–1.58 (6H, m), 1.37 (2H, s), 1.84 (2H, m), 2.69 (2H, t, J=7 Hz), 3.35 (2H, t, J=7 Hz), 7.29 (1H, dt, J=1&8 Hz), 7.42 (1H, dt, J=1&8 Hz), 7.76 (1H, dd, J=1&8 Hz), 7.87 (1H, d, J=7 Hz).

Reference Example 47

A mixture of N-[4-(N-acetyl-N-phenylamino)butyl]phthalimide (9.2 g), hydrazine monohydrate (10 ml) and ethanol (200 ml) was heated under reflux for 1 hour. The deposited crystals were separated by filtration, and the filtrate was concentrated under reduced pressure to obtain 4-(N-acetyl-N-phenylamino)butylamine (4.55 g, 80.7%) as an oil.

NMR (δ ppm in CDCl₃): 1.35–1.65 (4H, m), 1.60 (2H, s), 1.83 (3H, s), 2.69 (2H, t, J=7 Hz), 3.71 (2H, t, J=7 Hz), 7.33–7.48 (3H, m).

What is claimed is:

1. A method for inhibiting squalene synthetase in a mammal which comprises administering to a mammal in need of such treatment an effective amount of a compound of the formula (VI)

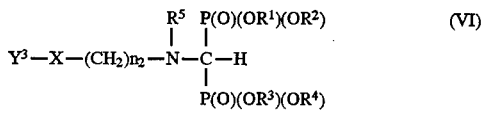

wherein $Y^3$ is an optionally substituted cyclic group, X is oxygen or optionally oxidized sulfur, $n_2$ is an integer of 2 to 15, $R^1$, $R^2$, $R^3$ and $R^4$ are hydrogen or lower alkyl, and $R^5$ is hydrogen or lower alkanoyl.

2. A method for treating hypercholesterolemia or coronary arteriosclerosis in a mammal, which comprises administering to a mammal in need of such treatment an effective amount of a compound of the formula (VI)

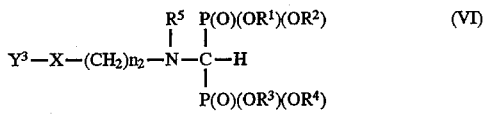

wherein $Y^3$ is an optionally substituted cyclic group, X is oxygen or optionally oxidized sulfur, $n_2$ is an integer of 2 to 15, $R^1$, $R^2$, $R^3$ and $R^4$ are hydrogen or lower alkyl, and $R^5$ is hydrogen or lower alkanoyl.

3. A method for inhibiting squalene synthetase in a mammal which comprises adminstering to a mammal in need of such treatment an effective amount of a compound of the formula (XIV)

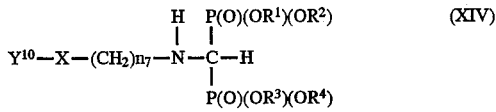

wherein $Y^{10}$ is phenyl, pyridyl or pyrimidinyl, X is oxygen or optionally oxidized sulfur, $n^7$ is an integer of 2 to 15, and $R^1$, $R^2$, $R^3$ and $R^4$ are hydrogen or lower alkyl.

4. A method for treating hypercholesterolemia or coronary arteriosclerosis in a mammal which comprises administering to a mammal in need of such treatment an effective amount of a compound of the formula (XIV)

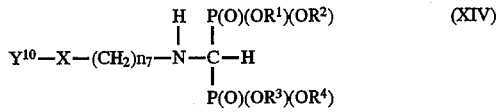

wherein $Y^{10}$ is phenyl, pyridyl or pyrimidinyl, X is oxygen or optionally oxidized sulfur, $n^7$ is an integer of 2 to 15, and $R^1$, $R^2$, $R^3$ and $R^4$ are hydrogen or lower alkyl.

5. A method for inhibiting squalene synthetase in a mammal according to claim 3, wherein n7 in the general formula (XIV) is an integer of 4 to 10.

6. A method for treating hypercholesterolemia or coronary arteriosclerosis in a mammal according to claim 4, wherein n7 in the formula (XIV) is an integer of 4 to 10.

7. A method for inhibiting squalene synthetase in a mammal as claimed in claim 6, which comprises administering to a mammal in need of such treatment an effective amount of 7-(phenylthio)heptyl aminomethylenebisphosphonic acid or a pharmaceutically acceptable salt thereof.

8. A method for treating hypercholesterolemia or coronary arteriosclerosis in a mammal as claimed in claim 4, which comprises administering to a mammal in need of such treatment an effective amount of 7-(phenylthio)heptyl aminoethylenebisphosphonic acid or a pharmaceutically acceptable salt thereof.

9. A method for inhibiting squalene synthetase in a mammal according to claim 3, which comprises administering to a mammal in need of such treatment an effective amount of 10-(phenylthio)decyl aminoethylenebisphosphonic acid or a pharmaceutically acceptable salt thereof.

10. A method for treating hypercholesterolemia or coronary arteriosclerosis in a mammal according to claim 4, which comprises administering to a mammal in need of such treatment an effective amount of 10-(phenylthio)decyl aminomethylenebisphosphonic acid or a pharmaceutically acceptable salt thereof.

11. A method for inhibiting squalene synthetase in a mammal according to claim 3, which comprises administering to a mammal in need of such treatment an effective amount of 9-(phenylsulfinyl)nonyl aminomethylenebisphosphonic acid or a pharmaceutically acceptable salt thereof.

12. A method for treating hypercholesterolemia or coronary arteriosclerosis in a mammal according to claim 4, which comprises administering to a mammal in need of such treatment an effective amount of 9-(phenylsulfinyl)nonyl aminomethylenebisphosphonic acid or a pharmaceutically acceptable salt thereof.

13. A method for inhibiting squalene synthetase in a mammal according to claim 3, which comprises administering to a mammal in need of such treatment an effective amount of 10-(phenylsulfinyl)decyl aminomethylenebisphosphonic acid or a pharmaceutically acceptable salt thereof.

14. A method for treating hypercholesterolemia or coronary arteriosclerosis in a mammal according to claim 4, which comprises administering to a mammal in need of such treatment an effective amount of 10-(phenylsulfinyl)decyl aminomethylenebisphosphonic acid or a pharmaceutically acceptable salt thereof.

15. A method for inhibiting squalene synthetase in a mammal according to claim 1, wherein $Y^3$ is (i) $C_{3-7}$ cycloalkyl, (ii) $C_{6-14}$ aryl which may optionally be substituted with straight or branched $C_{1-6}$ alkyl, halogen or methylenedioxy and optionally form a condensed ring with a 5 to 6 membered aromatic heterocycle containing 1 to 4 nitrogen atoms or (iii) a 5 to 6 membered aromatic heterocyclic group containing 1 to 2 nitrogen atoms and one sulfur atom or 5 to 6 membered aromatic heterocyclic group containing 1 to 4 nitrogen atoms each of which may optionally be substituted with straight or branched $C_{1-6}$ alkyl and optionally form a condensed ring with a benzene ring.

16. A method for treating hypercholesterolemia or coronary arteriosclerosis in a mammal according to claim 2, wherein $Y^3$ is (i) $C_{3-7}$ cycloalkyl, (ii) $C_{6-14}$ aryl which may optionally be substituted with straight or branched $C_{1-6}$ alkyl, halogen or methylenedioxy and optionally form a condensed ring with a 5 to 6 membered aromatic heterocycle containing 1 to 4 nitrogen atoms or (iii) a 5 to 6 membered aromatic heterocyclic group containing 1 to 2 nitrogen atoms and one sulfur atom or 5 to 6 membered aromatic heterocyclic group containing 1 to 4 nitrogen atoms each of which may optionally be substituted with straight or branched $C_{1-6}$ alkyl and optionally form a condensed ring with a benzene ring.

17. A method for inhibiting squalene synthetase in a mammal according to claim 1, wherein $Y^3$ is (i) phenyl or (ii) a 5 to 6 membered aromatic heterocyclic group containing 1 to 2 nitrogen atoms and one sulfur atom or 5 to 6 membered aromatic heterocyclic group containing 1 to 4 nitrogen atoms each of which may optionally be substituted with $C_{1-4}$ alkyl.

18. A method for treating hypercholesterolemia or coronary arteriosclerosis in a mammal according to claim 2, wherein $Y_3$ is (i) phenyl or (ii) a 5 to 6 membered aromatic heterocyclic group containing 1 to 2 nitrogen atoms and one sulfur atom or 5 to 6 membered aromatic heterocyclic group containing 1 to 4 nitrogen atoms each of which may optionally be substituted with $C_{1-4}$ alkyl.

19. A method for inhibiting squalene synthetase in a mammal which comprises administering to a mammal in need of such treatment an effective amount of disodium 6-(4-methoxybenzylthio)hexylaminomethylenebisphosphonate.

20. A method for treating hypercholesterolemia or coronary arteriosclerosis in a mammal which comprises administering to a mammal in need of such treatment an effective amount of disodium 6-(4-methoxybenzylthio) hexylaminomethylenebisphosphonate.

21. A method for inhibiting squalene synthetase in a mammal which comprises administering to a mammal in need of such treatment an effective amount of disodium 8-(2-pyrimidinylthio)octylaminomethylenebisphosphonate.

22. A method for treating hypercholesterolemia or coronary arteriosclerosis in a mammal which comprises administering to a mammal in need of such treatment an effective amount of disodium 8-(2-pyrimidinylthio)octylaminomethylenebisphosphonate.

23. A method for inhibiting squalene synthetase in a mammal which comprises administering to a mammal in need of such treatment an effective amount of 9-(2-pyrimidinylthio)nonylaminomethylenebisphosphonic acid di[tris(hydroxymethyl)aminomethane] salt.

24. A method for treating hypercholesterolemia or coronary arteriosclerosis in a mammal which comprises administering to a mammal in need of such treatment an effective amount of 9-(2-pyrimidinylthio)nonylaminomethylenebisphosphonic acid di[tris(hydroxymethyl)aminomethane] salt.

* * * * *